United States Patent
Green et al.

(10) Patent No.: US 11,478,529 B2
(45) Date of Patent: Oct. 25, 2022

(54) SRPX FOR TREATMENT OF CANCER

(71) Applicant: University of Massachusetts, Boston, MA (US)

(72) Inventors: Michael R. Green, Boylston, MA (US); Guangping Gao, Westborough, MA (US); Manas Kumar Santra, Pune (IN); Sanchita Bhatnagar, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 371 days.

(21) Appl. No.: 16/815,356

(22) Filed: Mar. 11, 2020

(65) Prior Publication Data
US 2020/0276266 A1    Sep. 3, 2020

Related U.S. Application Data

(63) Continuation of application No. 15/985,992, filed on May 22, 2018, now Pat. No. 10,624,951, which is a continuation of application No. 15/074,714, filed on Mar. 18, 2016, now Pat. No. 10,130,679, which is a continuation of application No. 14/240,813, filed as application No. PCT/US2012/055641 on Sep. 14, 2012, now Pat. No. 9,290,744.

(60) Provisional application No. 61/534,655, filed on Sep. 14, 2011.

(51) Int. Cl.
| | | |
|---|---|---|
| A61K 38/17 | (2006.01) | |
| A61K 35/12 | (2015.01) | |
| A61K 38/16 | (2006.01) | |
| A61K 48/00 | (2006.01) | |
| C12N 9/08  | (2006.01) | |

(52) U.S. Cl.
CPC .......... *A61K 38/1709* (2013.01); *A61K 35/12* (2013.01); *A61K 38/16* (2013.01); *A61K 48/005* (2013.01); *C12N 9/0065* (2013.01); *A61K 48/00* (2013.01)

(58) Field of Classification Search
None
See application file for complete search history.

(56) References Cited

U.S. PATENT DOCUMENTS

| 6,998,117 B1 | 2/2006 | Roth et al. |
| 2011/0052677 A1 | 3/2011 | Imhof et al. |

OTHER PUBLICATIONS

EP Extended European Search Report for corresponding European Application No. 12831511.6, dated May 26, 2015 (9 pages).
EP Office Action in European Application No. 12831511.6, dated Mar. 16, 2017.
http://en.wikipedia.org/wiki/P53, authors unknown, published by Wikipedia, San Francisco, CA, downloaded Apr. 18, 2015, downloaded as PDF, 21 pages long.
Kim et al., Down-Regulation of drs mRNA in Human.
Kirkitadze, Marina .D. and Barlow, Paul N., "Structure and flexibility of the multiple domain proteins that regulate complement activation", Immunological Reviews, vol. 180, pp. 146-161 (2001).
Manickan, et al. (2006) "Rapid Kupffer cell death after intravenous injection of adenovirus vectors", Molecular Therapy, 13(1):108-17.
Miljkovic-Licina et al., "Sushi repeat protein X-linked 2, a novel mediator of angiogenesis," FASEB J., Dec. 2009, 23:4105-4116.
Mukaisho et al., "Down-regulation of drs mRNA in Colorectal Neoplasms," Jpn. J. Cancer Res., 2002, 93:888-893.
Norman et al., "Three-dimensional Structure of a Complement Control Protein Module in Solution," J. Mol. Biol., col. 219, pp. 717-725 (1991).
Pawlowski et al., "A widespread peroxiredoxin-like domain present in tumor suppression- and progression-implicated proteins", BMC Genomics, vol. 11:590 (18 pages).
PCT International Preliminary Report on Patentability, International Application No. PCT/US2012/055641, dated Mar. 27, 2014 (7 pages).
PCT International Search Report and Written Opinion in International Application No. PCT/US2012/055641, dated Mar. 13, 2013, 12 pages.
Sandler et al., "Paclitaxel-Carboplatin Alone or with Bevacizumab for Non-Small-Cell Lung Cancer", The New England Journal of Medicine, vol. 355, No. 24, pp. 2542-2550 (Dec. 14, 2006).
Schiller et al., "Comparison of Four Chemotherapy Regimens for Advanced Non-Small-Cell Lung Cancer", The New England Journal of Medicine, vol. 346, No. 2, pp. 92-98 (Jan. 10, 2002).
Shimakage et al., "Downregulation of drs mRNA expression is associated with the progression of adult T-cell leukemia/lymphoma," Int J Oncol., 2007, 30:1343-1348.
Shimakage et al., "Down-Regulation of drs mRNA in Human Colon Adenocarcinomas," Int J Cancer, 2000, 87:5-11.
Shimakage et al., "Downregulation of drs tumor suppressor gene in highly malignant human pulmonary neuroendocrine tumors," Oncol Rep., 2009, 21:1367-1372.
Shimakage et al., "Expression of drs mRNA in Human Lung Adenocarcinomas," Human Pathol., Jun. 2002, 33(6):615-619.
Tambe et al., "The drs tumor suppressor is involved in the maturation process of autophagy induced by low serum," Cancer Lett., 2009, 283:74-83.
Tambe et al., "Tumor prone phenotype of mice deficient in a novel apoptosis-inducing gene, drs," Carcinogenesis, 2007, 28(4):777-784.
Tanaka et al., "SRPX2 is overexpressed in gastric cancer and promotes cellular migration and adhesion," Int J Cancer, 2009, 124:1072-1080.
Yamashita et al., "Suppression of anchorage-independent growth of human cancer cell lines by the drs gene," Oncogene, 1999, 18:4777-4787.

*Primary Examiner* — Robert M Kelly
(74) *Attorney, Agent, or Firm* — Fish & Richardson P.C.

(57) ABSTRACT

Methods of treating a tumor in a subject include identifying a subject having, at risk for, or suspected of having a tumor, and administering to the subject an effective amount of an SRPX.

18 Claims, 14 Drawing Sheets

Specification includes a Sequence Listing.

```
   1 attaggctgc gcgctcgctc gctcactgag gccgcccggg caaagcccgg gcgtcgggcg
  61 acctttggtc gcccggcctc agtgagcgag cgagcgcgca gagagggagt ggccaactcc
 121 atcactaggg gttccttgta gttaatgatt aacccgccat gctacttatc taccagggta
 181 atggggatcc tctagaacta tagctagcat gcctgcaggc tgaccgccca acgaccccg
 241 cccattgacg tcaataatga cgtatgttcc catagtaacg ccaataggga ctttccattg
 301 acgtcaatgg gtggagtatt tacggtaaac tgcccacttg gcagtacatc aagtgtatca
 361 tatgccaagt ccgcccccta ttgacgtcaa tgacggtaaa tggcccgcct ggcattatgc
 421 ccagtacatg accttacggg actttcctac ttggcagtac atctacgtat tagtcatcgc
 481 tattaccatg gtgatgcggt tttggcagta caccaatggg cgtggatagc ggtttgactc
 541 acgggatttt ccaagtctcc accccattga cgtcaatggg agtttgtttt ggcaccaaaa
 601 tcaacgggac tttccaaaat gtcgtaataa ccccgccccg ttgacgcaaa tgggcggtag
 661 gcgtgtacgg tgggaggtct atataagcag agctcgttta gtgaaccgtc agatcactag
 721 aagctttatt gcggtagttt atcacagtta aattgctaac gcagtcagtg cttctgacac
 781 aacagtctcg aacttaagct gcagaagttg gtcgtgaggc actgggcagg taagtatcaa
 841 ggttacaaga caggtttaag gagaccaata gaaactgggc ttgtcgagac agagaagact
 901 cttgcgtttc tgataggcac ctattggtct tactgacatc cactttgcct ttctctccac
 961 aggtgtccac tcccagttca attacagctc ttaaggctag agtacttaat acgactcact
1021 ataggctagc ctcgagaatt cacgcgtggt acggtaccat gatggagaca gacacactcc
1081 tgctatgggt actgctgctc tgggttccag gttccactgg tgacgcggcc cagccggcca
1141 ggcgcgcgcg ccgtacgaag cttgactcac cactagaaga cgatgaagtc gggtattcac
1201 accctagata taaagatacc ccgtggtgct cccccatcaa ggtgaagtat ggggatgtgt
1261 actgcagggc ccctcaagga ggatactaca aaacagccct gggaaccagg tgcgacattc
1321 gctgccagaa gggctacgag ctgcatggct cttccctact gatctgccag tcaaacaaac
1381 gatggtctga caaggtcatc tgcaaacaaa agcgatgtcc taccttgcc atgccagcaa
1441 atggagggtt taagtgtgta gatggtgcct actttaactc ccggtgtgag tattattgtt
1501 caccaggata cacgttgaaa ggggagcgga ccgtcacatg tatggacaac aaggcctgga
1561 gcggccggcc agcctcctgt gtggatatgg aacctcctag aatcaagtgc caagtgtga
1621 aggaacgcat tgcagaaccc aacaaactga cagtccgggt gtcctggag acaccgaag
1681 gaagagacac agcagatgga attcttactg atgtcattct aaaaggcctc cccccaggct
1741 ccaactttcc agaaggagac cacaagatcc agtacacagt ctatgacaga gctgagaata
1801 agggcacttg caaatttcga gttaaagtaa gagtcaaacg ctgtggcaaa ctcaatgccc
1861 cagagaatgg ttacatgaag tgctccagcg acggtgataa ttatggagcc acctgtgagt
1921 tctcctgcat cggcggctat gagctccagg gtagccctgc ccgagtatgt caatccaacc
1981 tggcttggtc tggcacggag cccacctgtg cagccatgaa cgtcaatgtg ggtgtcagaa
2041 cggcagctgc acttctggat cagttttatg agaaaggag actcctcatt gtgtccacac
2101 ccacagcccg aaacctcctt taccggctcc agctaggaat gctgcagcaa gcacagtgtg
2161 gccttgatct tcgacacatc accgtggtgg agctggtggg tgtgttcccg actctcattg
2221 gcaggatagg agcaaagatt atgcctccag ccctagcgct gcagctcagg ctgttgctgc
2281 gaatcccact ctactccttc agtatggtgc tagtggataa gcatggcatg acaaagagc
2341 gctatgtctc cctggtgatg cctgtggccc tgttcaacct gattgacact ttcccttga
2401 gaaagaaga gatggtccta caagccgaaa tgagccagac ctgtaacacc gctcgaggag
2461 ggcccgaaca aaaactcatc tcagaagaga atctgaatag cgccgtcgac catcatcatc
2521 atcatcattg aggtaccctc tagagtcgac ccgggcggcc tcgaggacgg ggtgaactac
2581 gcctgaggat ccgatctttt tccctctgcc aaaaattatg gggacatcat gaagcccctt
2641 gagcatctga cttctggcta taaaggaaa tttattttca ttgcaatagt gtgttggaat
2701 tttttgtgtc tctcactcgg aagcaattcg ttgatctgaa tttcgaccac ccataatacc
2761 cattaccctg gtagataagt agcatggcgg gttaatcatt aactacaagg accccctagt
2821 gatggagttg gccactccct ctctgcgcgc tcgctcgctc actgaggccg ggcgaccaaa
2881 ggtcgcccga cgcccgggct ttgcccgggc ggcctcagtg agcgagcgag cgcgcagcct
2941 taattaacct aattcactgg ccgtcgtttt acaacgtcgt gactgggaaa accctggcgt
```

FIG. 4C

```
3001 tacccaactt aatcgccttg cagcacatcc cccttttcgcc agctggcgta atagcgaaga
3061 ggcccgcacc gatcgccctt cccaacagtt gcgcagcctg aatggcgaat gggacgcgcc
3121 ctgtagcggc gcattaagcg cggcgggtgt ggtggttacg cgcagcgtga ccgctacact
3181 tgccagcgcc ctagcgcccg ctcctttcgc tttcttccct tcctttctcg ccacgttcgc
3241 cggctttccc cgtcaagctc taaatcgggg gctcccttta gggttccgat ttagtgcttt
3301 acggcacctc gaccccaaaa aacttgatta gggtgatggt tcacgtagtg ggccatcgcc
3361 ctgatagacg gttttcgcc ctttgacgtt ggagtccacg ttctttaata gtggactctt
3421 gttccaaact ggaacaacac tcaaccctat ctcggtctat tcttttgatt tataagggat
3481 tttgccgatt tcggcctatt ggttaaaaaa tgagctgatt taacaaaaat ttaacgcgaa
3541 ttttaacaaa atattaacgc ttacaattta ggtggcactt tcggggaaa tgtgcgcgga
3601 accccatttt gtttattttt ctaaatacat tcaaatatgt atccgctcat gagacaataa
3661 ccctgataaa tgcttcaata atattgaaaa aggaagagta tgagtattca acatttccgt
3721 gtcgcccta ttccttttt tgcggcattt tgccttcctg ttttgctca cccagaaacg
3781 ctggtgaaag taaaagatgc tgaagatcag ttgggtgcac gagtgggtta catcgaactg
3841 gatctcaaca gcggtaagat ccttgagagt tttcgccccg aagaacgttt tccaatgatg
3901 agcactttta aagttctgct atgtggcgcg gtattatccc gtattgacgc cgggcaagag
3961 caactcggtc gccgcataca ctattctcag aatgacttgg ttgagtactc accagtcaca
4021 gaaaagcatc ttacggatgg catgacagta agagaattat gcagtgctgc cataaccatg
4081 agtgataaca ctgcggccaa cttacttctg acaacgatcg gaggaccgaa ggagctaacc
4141 gcttttttgc acaacatggg ggatcatgta actcgccttg atcgttggga accggagctg
4201 aatgaagcca taccaaacga cgagcgtgac accacgatgc ctgtagcaat ggcaacaacg
4261 ttgcgcaaac tattaactgg cgaactactt actctagctt cccggcaaca attaatagac
4321 tggatggagg cggataaagt tgcaggacca cttctgcgct cggcccttcc ggctggctgg
4381 tttattgctg ataaatctgg agccggtgag cgtgggtctc gcggtatcat tgcagcactg
4441 gggccagatg gtaagccctc ccgtatcgta gttatctaca cgacggggag tcaggcaact
4501 atggatgaac gaaatagaca gatcgctgag ataggtgcct cactgattaa gcattggtaa
4561 ctgtcagacc aagtttactc atatatactt tagattgatt taaaacttca ttttaattt
4621 aaaaggatct aggtgaagat cctttttgat aatctcatga ccaaaatccc ttaacgtgag
4681 ttttcgttcc actgagcgtc agaccccgta gaaaagatca aggatcttc ttgagatcct
4741 ttttttctgc gcgtaatctg ctgcttgcaa acaaaaaaac caccgctacc agcggtggtt
4801 tgtttgccgg atcaagagct accaactctt tttccgaagg taactggctt cagcagagcg
4861 cagataccaa atactgttct tctagtgtag ccgtagttag gccaccactt caagaactct
4921 gtagcaccgc ctacatacct cgctctgcta atcctgttac cagtggctgc tgccagtggc
4981 gataagtcgt gtcttaccgg gttggactca agacgatagt taccggataa ggcgcagcgg
5041 tcgggctgaa cggggggttc gtgcacacag cccagcttgg agcgaacgac ctacaccgaa
5101 ctgagatacc tacagcgtga gctatgagaa agcgccacgc ttcccgaagg gagaaaggcg
5161 gacaggtatc cggtaagcgg cagggtcgga acaggagagc gcacgaggga gcttccaggg
5221 ggaaacgcct ggtatcttta tagtcctgtc gggtttcgcc acctctgact tgagcgtcga
5281 tttttgtgat gctcgtcagg gggcggagc ctatggaaaa acgccagcaa gcggcctttt
5341 ttacggttcc tggccttttg ctggcctttt gctcacatgt tctttcctgc gttatcccct
5401 gattctgtgg ataaccgtat taccgccttt gagtgagctg ataccgctcg ccgcagccga
5461 acgaccgagc gcagcgagtc agtgagcgag gaagcggaag agcgcccaat acgcaaaccg
5521 cctctccccg cgcgttggcc gattcattaa tgcagctggc acgacaggtt tcccgactgg
5581 aaagcgggca gtgagcgcaa cgcaattaat gtgagttagc tcactcatta ggcacccag
5641 gctttacact ttatgcttcc ggctcgtatg ttgtgtggaa ttgtgagcgg ataacaattt
5701 cacacaggaa acagctatga ccatgattac gccagattta attaaggcct ta
                                SEQ ID NO: 5
```

FIG. 4D

```
   1 attaggctgc gcgctcgctc gctcactgag gccgcccggg caaagcccgg gcgtcgggcg
  61 acctttggtc gcccggcctc agtgagcgag cgagcgcgca gagagggagt ggccaactcc
 121 atcactaggg gttccttgta gttaatgatt aacccgccat gctacttatc taccagggta
 181 atggggatcc tctagaacta tagctagcat gcctgcaggc tgaccgccca acgaccccg
 241 cccattgacg tcaataatga cgtatgttcc catagtaacg ccaatagggn ctttccattg
 301 acgtcaatgg gtggagtatt tacggtaaac tgcccacttg gcagtacatc aagtgtatca
 361 tatgccaagt ccgcccccta ttgacgtcaa tgacggtaaa tggcccgcct ggcattatgc
 421 ccagtacatg accttacggg actttcctac ttggcagtac atctacgtat tagtcatcgc
 481 tattaccatg gtgatgcggt tttggcagta caccaatggg cgtggatagc ggtttgactc
 541 acggggattt ccaagtctcc accccattga cgtcaatggg agtttgtttt ggcaccaaaa
 601 tcaacgggac tttccaaaat gtcgtaataa cccgcccg ttgacgcaaa tgggcggtag
 661 gcgtgtacgg tgggaggtct atataagcag agctcgttta gtgaaccgtc agatcactag
 721 aagctttatt gcggtagttt atcacagtta aattgctaac gcagtcagtg cttctgacac
 781 aacagtctcg aacttaagct gcagaagttg gtcgtgaggc actgggcagg taagtatcaa
 841 ggttacaaga caggtttaag gagaccaata gaaactgggc ttgtcgagac agaagact
 901 cttgcgtttc tgataggcac ctattggtct tactgacatc cactttgcct ttctctccac
 961 aggtgtccac tcccagttca attacagctc ttaaggctag agtacttaat acgactcact
1021 ataggctagc ctcgagaatt cacgcgtggt acggtaccat ggggagcccc gcacatcggc
1081 ccgcgctgct gctgctgctg ccgcctctgc tgctgctgct gctgctgcgc gtcccgccca
1141 gccgcagctt cccaggatcg ggagactcac cactagaaga cgatgaagtc gggtattcac
1201 accctagata taaagatacc ccgtggtgct cccccatcaa ggtgaagtat ggggatgtgt
1261 actgcagggc ccctcaagga ggatactaca aaacagccct gggaaccagg tgcgacattc
1321 gctgccagaa gggctacgag ctgcatggct cttccctact gatctgccag tcaaacaaac
1381 gatggtctga caaggtcatc tgcaaacaaa agcgatgtcc taccccttgcc atgccagcaa
1441 atggagggtt taagtgtgta gatggtgcct actttaactc ccggtgtgag tattattgtt
1501 caccaggata cacgttgaaa ggggagcgga ccgtcacatg tatggacaac aaggcctgga
1561 gcggccggcc agcctcctgt gtggatatgg aacctcctag aatcaagtgc caagtgtga
1621 aggaacgcat tgcagaaccc aacaaactga cagtccgggt gtcctggag acaccgaag
1681 gaagagacac agcagatgga attcttactg atgtcattct aaaaggcctc ccccaggct
1741 ccaactttcc agaaggagac cacaagatcc agtacacagt ctatgacaga gctgagaata
1801 agggcacttg caaatttcga gttaaagtaa gagtcaaacg ctgtggcaaa ctcaatgccc
1861 cagagaatgg ttacatgaag tgctccagcg acggtgataa ttatggagcc acctgtgagt
1921 tctcctgcat cggcggctat gagctccagg gtagccctgc ccgagtatgt caatccaacc
1981 tggcttggtc tggcacggag cccacctgtg cagccatgaa cgtcaatgtg ggtgtcagaa
2041 cggcagctgc acttctggat cagttttatg agaaaggag actcctcatt gtgtccacac
2101 ccacagcccg aaacctcctt taccggctcc agctaggaat gctgcagcaa gcacagtgtg
2161 gccttgatct tcgacacatc accgtggtgg agctggtggg tgtgttcccg actctcattg
2221 gcaggatagg agcaaagatt atgcctccag ccctagcgct gcagctcagg ctgttgctgc
2281 gaatccact ctactccttc agtatggtgc tagtggataa gcatggcatg acaaagagc
2341 gctatgtctc cctggtgatg cctgtggccc tgttcaacct gattgacact tttcccttga
2401 gaaagaaga gatggtccta caagccgaaa tgagccagac ctgtaacacc gaacaaaaac
2461 tcatctcaga agaggatctg aatagcgccg tcgaccatca tcatcatcat cattgaggta
2521 ccctctagag tcgacccggg cggctcgag gacggggtga actacgcctg aggatccgat
2581 cttttccct ctgccaaaaa ttatgggac atcatgaagc cccttgagca tctgacttct
2641 ggctaataaa ggaaatttat tttcattgca atagtgtgtt ggaatttttt gtgtctctca
2701 ctcggaagca attcgttgat ctgaatttcg accaccata atacccatta ccctggtaga
2761 taagtagcat ggcgggttaa tcattaacta caaggaaccc ctagtgatgg agttggccac
2821 tccctctctg cgcgctcgct cgctcactga ggccgggcga ccaaaggtcg cccgacgccc
2881 gggctttgcc cgggcggcct cagtgagcga gcgagcgcgc agccttaatt aacctaattc
2941 actggccgtc gttttacaac gtcgtgactg ggaaaaccct ggcgttaccc aacttaatcg
```

FIG. 5C

```
3001 ccttgcagca catccccctt tcgccagctg gcgtaatagc gaagaggccc gcaccgatcg
3061 cccttcccaa cagttgcgca gcctgaatgg cgaatgggac gcgccctgta gcggcgcatt
3121 aagcgcggcg ggtgtggtgg ttacgcgcag cgtgaccgct acacttgcca gcgccctagc
3181 gcccgctcct ttcgctttct tcccttcctt tctcgccacg ttcgccggct ttccccgtca
3241 agctctaaat cgggggctcc ctttagggtt ccgatttagt gctttacggc acctcgaccc
3301 caaaaaactt gattagggtg atggttcacg tagtgggcca tcgccctgat agacggtttt
3361 tcgccctttg acgttggagt ccacgttctt taatagtgga ctcttgttcc aaactggaac
3421 aacactcaac cctatctcgg tctattcttt tgatttataa gggattttgc cgatttcggc
3481 ctattggtta aaaaatgagc tgatttaaca aaaatttaac gcgaatttta acaaaatatt
3541 aacgcttaca atttaggtgg cacttttcgg ggaaatgtgc gcggaacccc tatttgttta
3601 tttttctaaa tacattcaaa tatgtatccg ctcatgagac aataaccctg ataaatgctt
3661 caataatatt gaaaaggaa gagtatgagt attcaacatt tccgtgtcgc ccttattccc
3721 ttttttgcgg cattttgcct tcctgttttt gctcacccag aaacgctggt gaaagtaaaa
3781 gatgctgaag atcagttggg tgcacgagtg ggttacatcg aactggatct caacagcggt
3841 aagatccttg agagttttcg ccccgaagaa cgttttccaa tgatgagcac ttttaaagtt
3901 ctgctatgtg gcgcggtatt atcccgtatt gacgccgggc aagagcaact cggtcgccgc
3961 atacactatt ctcagaatga cttggttgag tactcaccag tcacagaaaa gcatcttacg
4021 gatggcatga cagtaagaga attatgcagt gctgccataa ccatgagtga taacactgcg
4081 gccaacttac ttctgacaac gatcggagga ccgaaggagc taaccgcttt tttgcacaac
4141 atgggggatc atgtaactcg ccttgatcgt tgggaaccgg agctgaatga agccatacca
4201 aacgacgagc gtgacaccac gatgcctgta gcaatggcaa caacgttgcg caaactatta
4261 actggcgaac tacttactct agcttccgg caacaattaa tagactggat ggaggcggat
4321 aaagttgcag gaccacttct gcgctcggcc cttccggctg gctggtttat tgctgataaa
4381 tctggagccg gtgagcgtgg gtctcgcggt atcattgcag cactggggcc agatggtaag
4441 ccctcccgta tcgtagttat ctacacgacg gggagtcagg caactatgga tgaacgaaat
4501 agacagatcg ctgagatagg tgcctcactg attaagcatt ggtaactgtc agaccaagtt
4561 tactcatata tactttagat tgatttaaaa cttcattttt aatttaaaag gatctaggtg
4621 aagatccttt tgataatct catgaccaaa atcccttaac gtgagttttc gttccactga
4681 gcgtcagacc ccgtagaaaa gatcaaagga tcttcttgag atcctttttt tctgcgcgta
4741 atctgctgct tgcaaacaaa aaaaccaccg ctaccagcgg tggtttgttt gccggatcaa
4801 gagctaccaa ctcttttttcc gaaggtaact ggcttcagca gagcgcagat accaaatact
4861 gttcttctag tgtagccgta gttaggccac cacttcaaga actctgtagc accgcctaca
4921 tacctcgctc tgctaatcct gttaccagtg gctgctgcca gtggcgataa gtcgtgtctt
4981 accgggttgg actcaagacg atagttaccg gataaggcgc agcggtcggg ctgaacgggg
5041 ggttcgtgca cacagcccag cttggagcga acgacctaca ccgaactgag atacctacag
5101 cgtgagctat gagaaagcgc cacgcttccc gaagggagaa aggcggacag gtatccggta
5161 agcggcaggg tcggaacagg agagcgcacg agggagcttc caggggggaaa cgcctggtat
5221 ctttatagtc ctgtcgggtt tcgccacctc tgacttgagc gtcgatttt gtgatgctcg
5281 tcagggggc ggagcctatg gaaaaacgcc agcaacgcgg cctttttacg gttcctggcc
5341 ttttgctggc cttttgctca catgttcttt cctgcgttat cccctgattc tgtggataac
5401 cgtattaccg cctttgagtg agctgatacc gctcgccgca gccgaacgac cgagcgcagc
5461 gagtcagtga gcgaggaagc ggaagagcgc ccaatacgca aaccgcctct ccccgcgcgt
5521 tggccgattc attaatgcag ctggcacgac aggtttcccg actggaaagc gggcagtgag
5581 cgcaacgcaa ttaatgtgag ttagctcact cattaggcac cccaggcttt cacttatg
5641 cttccggctc gtatgttgtg tggaattgtg agcggataac aatttcacac aggaaacagc
5701 tatgaccatg attacgccag atttaattaa ggcctta
                                SEQ ID NO:6
```

FIG. 5D

SEQUENCE LISTING

<160> NUMBER OF SEQ ID NOS: 8

<210> SEQ ID NO 1
<211> LENGTH: 429
<212> TYPE: PRT
<213> ORGANISM: Homo sapien

<400> SEQUENCE: 1

```
Asp Ser Pro Leu Glu Asp Asp Glu Val Gly Tyr Ser His Pro Arg Tyr
1               5                   10                  15

Lys Asp Thr Pro Trp Cys Ser Pro Ile Lys Val Lys Tyr Gly Asp Val
            20                  25                  30

Tyr Cys Arg Ala Pro Gln Gly Gly Tyr Tyr Lys Thr Ala Leu Gly Thr
        35                  40                  45

Arg Cys Asp Ile Arg Cys Gln Lys Gly Tyr Glu Leu His Gly Ser Ser
    50                  55                  60

Leu Leu Ile Cys Gln Ser Asn Lys Arg Trp Ser Asp Lys Val Ile Cys
65                  70                  75                  80

Lys Gln Lys Arg Cys Pro Thr Leu Ala Met Pro Ala Asn Gly Gly Phe
                85                  90                  95

Lys Cys Val Asp Gly Ala Tyr Phe Asn Ser Arg Cys Glu Tyr Tyr Cys
            100                 105                 110

Ser Pro Gly Tyr Thr Leu Lys Gly Glu Arg Thr Val Thr Cys Met Asp
        115                 120                 125

Asn Lys Ala Trp Ser Gly Arg Pro Ala Ser Cys Val Asp Met Glu Pro
    130                 135                 140

Pro Arg Ile Lys Cys Pro Ser Val Lys Glu Arg Ile Ala Glu Pro Asn
145                 150                 155                 160

Lys Leu Thr Val Arg Val Ser Trp Glu Thr Pro Glu Gly Arg Asp Thr
                165                 170                 175

Ala Asp Gly Ile Leu Thr Asp Val Ile Leu Lys Gly Leu Pro Pro Gly
            180                 185                 190

Ser Asn Phe Pro Glu Gly Asp His Lys Ile Gln Tyr Thr Val Tyr Asp
        195                 200                 205

Arg Ala Glu Asn Lys Gly Thr Cys Lys Phe Arg Val Lys Val Arg Val
    210                 215                 220

Lys Arg Cys Gly Lys Leu Asn Ala Pro Glu Asn Gly Tyr Met Lys Cys
225                 230                 235                 240

Ser Ser Asp Gly Asp Asn Tyr Gly Ala Thr Cys Glu Phe Ser Cys Ile
                245                 250                 255

Gly Gly Tyr Glu Leu Gln Gly Ser Pro Ala Arg Val Cys Gln Ser Asn
```

```
                   260                 265                 270
Leu Ala Trp Ser Gly Thr Glu Pro Thr Cys Ala Ala Met Asn Val Asn
            275                 280                 285

Val Gly Val Arg Thr Ala Ala Ala Leu Leu Asp Gln Phe Tyr Glu Lys
        290                 295                 300

Arg Arg Leu Leu Ile Val Ser Thr Pro Thr Ala Arg Asn Leu Leu Tyr
305                 310                 315                 320

Arg Leu Gln Leu Gly Met Leu Gln Gln Ala Gln Cys Gly Leu Asp Leu
                325                 330                 335

Arg His Ile Thr Val Val Glu Leu Val Gly Val Phe Pro Thr Leu Ile
                340                 345                 350

Gly Arg Ile Gly Ala Lys Ile Met Pro Pro Ala Leu Ala Leu Gln Leu
            355                 360                 365

Arg Leu Leu Leu Arg Ile Pro Leu Tyr Ser Phe Ser Met Val Leu Val
        370                 375                 380

Asp Lys His Gly Met Asp Lys Glu Arg Tyr Val Ser Leu Val Met Pro
385                 390                 395                 400

Val Ala Leu Phe Asn Leu Ile Asp Thr Phe Pro Leu Arg Lys Glu Glu
                405                 410                 415

Met Val Leu Gln Ala Glu Met Ser Gln Thr Cys Asn Thr
                420                 425

<210> SEQ ID NO 2
<211> LENGTH: 464
<212> TYPE: PRT
<213> ORGANISM: Homo sapien

<400> SEQUENCE: 2

Met Gly Ser Pro Ala His Arg Pro Ala Leu Leu Leu Leu Leu Pro Pro
1               5                   10                  15

Leu Leu Leu Leu Leu Leu Arg Val Pro Pro Ser Arg Ser Phe Pro
            20                  25                  30

Gly Ser Gly Asp Ser Pro Leu Glu Asp Asp Glu Val Gly Tyr Ser His
        35                  40                  45

Pro Arg Tyr Lys Asp Thr Pro Trp Cys Ser Pro Ile Lys Val Lys Tyr
    50                  55                  60

Gly Asp Val Tyr Cys Arg Ala Pro Gln Gly Gly Tyr Tyr Lys Thr Ala
65                  70                  75                  80

Leu Gly Thr Arg Cys Asp Ile Arg Cys Gln Lys Gly Tyr Glu Leu His
                85                  90                  95

Gly Ser Ser Leu Leu Ile Cys Gln Ser Asn Lys Arg Trp Ser Asp Lys
            100                 105                 110

Val Ile Cys Lys Gln Lys Arg Cys Pro Thr Leu Ala Met Pro Ala Asn
        115                 120                 125

Gly Gly Phe Lys Cys Val Asp Gly Ala Tyr Phe Asn Ser Arg Cys Glu
    130                 135                 140

Tyr Tyr Cys Ser Pro Gly Tyr Thr Leu Lys Gly Glu Arg Thr Val Thr
145                 150                 155                 160

Cys Met Asp Asn Lys Ala Trp Ser Gly Arg Pro Ala Ser Cys Val Asp
                165                 170                 175

Met Glu Pro Pro Arg Ile Lys Cys Pro Ser Val Lys Glu Arg Ile Ala
            180                 185                 190

Glu Pro Asn Lys Leu Thr Val Arg Val Ser Trp Glu Thr Pro Glu Gly
        195                 200                 205
```

Arg Asp Thr Ala Asp Gly Ile Leu Thr Asp Val Ile Leu Lys Gly Leu
210                 215                 220

Pro Pro Gly Ser Asn Phe Pro Glu Gly Asp His Lys Ile Gln Tyr Thr
225                 230                 235                 240

Val Tyr Asp Arg Ala Glu Asn Lys Gly Thr Cys Lys Phe Arg Val Lys
                245                 250                 255

Val Arg Val Lys Arg Cys Gly Lys Leu Asn Ala Pro Glu Asn Gly Tyr
            260                 265                 270

Met Lys Cys Ser Ser Asp Gly Asp Asn Tyr Gly Ala Thr Cys Glu Phe
            275                 280                 285

Ser Cys Ile Gly Gly Tyr Glu Leu Gln Gly Ser Pro Ala Arg Val Cys
290                 295                 300

Gln Ser Asn Leu Ala Trp Ser Gly Thr Glu Pro Thr Cys Ala Ala Met
305                 310                 315                 320

Asn Val Asn Val Gly Val Arg Thr Ala Ala Ala Leu Leu Asp Gln Phe
                325                 330                 335

Tyr Glu Lys Arg Arg Leu Leu Ile Val Ser Thr Pro Thr Ala Arg Asn
            340                 345                 350

Leu Leu Tyr Arg Leu Gln Leu Gly Met Leu Gln Gln Ala Gln Cys Gly
            355                 360                 365

Leu Asp Leu Arg His Ile Thr Val Val Glu Leu Val Gly Val Phe Pro
370                 375                 380

Thr Leu Ile Gly Arg Ile Gly Ala Lys Ile Met Pro Pro Ala Leu Ala
385                 390                 395                 400

Leu Gln Leu Arg Leu Leu Arg Ile Pro Leu Tyr Ser Phe Ser Met
                405                 410                 415

Val Leu Val Asp Lys His Gly Met Asp Lys Glu Arg Tyr Val Ser Leu
            420                 425                 430

Val Met Pro Val Ala Leu Phe Asn Leu Ile Asp Thr Phe Pro Leu Arg
            435                 440                 445

Lys Glu Glu Met Val Leu Gln Ala Glu Met Ser Gln Thr Cys Asn Thr
        450                 455                 460

<210> SEQ ID NO 3
<211> LENGTH: 2962
<212> TYPE: DNA
<213> ORGANISM: Artificial Sequence
<220> FEATURE:
<223> OTHER INFORMATION: synthetically-generated vector

<400> SEQUENCE: 3
attaggctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc taccagggta     180
atggggatcc tctagaacta tagctagcat gcctgcaggc tgaccgccca acgacccccg     240
cccattgacg tcaataatga cgtatgttcc catagtaacg ccaataggga ctttccattg     300
acgtcaatgg gtggagtatt tacggtaaac tgcccacttg gcagtacatc aagtgtatca     360
tatgccaagt ccgcccccta ttgacgtcaa tgacggtaaa tggcccgcct ggcattatgc     420
ccagtacatg accttacggg actttcctac ttggcagtac atctacgtat tagtcatcgc     480
tattaccatg gtgatgcggt tttggcagta caccaatggg cgtggatagc ggtttgactc     540
acggggattt ccaagtctcc accccattga cgtcaatggg agtttgtttt ggcaccaaaa     600
tcaacgggac tttccaaaat gtcgtaataa ccccgccccg ttgacgcaaa tgggcggtag     660

```
gcgtgtacgg tgggaggtct atataagcag agctcgttta gtgaaccgtc agatcactag      720
aagctttatt gcggtagttt atcacagtta aattgctaac gcagtcagtg cttctgacac      780
aacagtctcg aacttaagct gcagaagttg gtcgtgaggc actgggcagg taagtatcaa      840
ggttacaaga caggtttaag gagaccaata gaaactgggc ttgtcgagac agagaagact      900
cttgcgtttc tgataggcac ctattggtct tactgacatc cactttgcct ttctctccac      960
aggtgtccac tcccagttca attacagctc ttaaggctag agtacttaat acgactcact     1020
ataggctagc ctcgagaatt cacgcgtggt acggtaccat gatggagaca gacacactcc     1080
tgctatgggt actgctgctc tgggttccag gttccactgg tgacgcggcc cagccggcca     1140
ggcgcgcgcg ccgtacgaag cttgactcac cactagaaga cgatgaagtc gggtattcac     1200
accctagata taaagatacc ccgtggtgct cccccatcaa ggtgaagtat ggggatgtgt     1260
actgcagggc ccctcaagga ggatactaca aaacagccct gggaaccagg tgcgacattc     1320
gctgccagaa gggctacgag ctgcatggct cttccctact gatctgccag tcaaacaaac     1380
gatggtctga caaggtcatc tgcaaacaaa agcgatgtcc taccctgtcc atgccagcaa     1440
atggagggtt taagtgtgta gatggtgcct actttaactc ccggtgtgag tattattgtt     1500
caccaggata cacgttgaaa ggggagcgga ccgtcacatg tatggacaac aaggcctgga     1560
gcggccggcc agcctcctgt gtggatatgg aacctcctag aatcaagtgc ccaagtgtga     1620
aggaacgcat tgcagaaccc aacaaactga cagtccgggt gtcctgggag acacccgaag     1680
gaagagacac agcagatgga attcttactg atgtcattct aaaaggcctc cccccaggct     1740
ccaactttcc agaaggagac cacaagatcc agtacacagt ctatgacaga gctgagaata     1800
agggcacttg caaatttcga gttaaagtaa gagtcaaacg ctgtggcaaa ctcaatgccc     1860
cagagaatgg ttacatgaag tgctccagcg acggtgataa ttatggagcc acctgtgagt     1920
tctcctgcat cggcggctat gagctccagg gtagccctgc cgagtatgt caatccaacc     1980 tggcttggtc tggcacggag cccacctgtg cagccatgaa cgtcaatgtg ggtgtcagaa     2040
cggcagctgc acttctggat cagttttatg agaaaaggag actcctcatt gtgtccacac     2100
ccacagcccg aaacctcctt taccggctcc agctaggaat gctgcagcaa gcacagtgtg     2160
gccttgatct tcgacacatc accgtggtgg agctggtggg tgtgttccg actctcattg     2220 gcaggatagg agcaaagatt atgcctccag ccctagcgct gcagctcagg ctgttgctgc     2280
gaatcccact ctactccttc agtatggtgc tagtggataa gcatggcatg gacaaagagc     2340
gctatgtctc cctggtgatg cctgtggccc tgttcaacct gattgacact tttcccttga     2400
gaaaagaaga gatggtccta caagccgaaa tgagccagac ctgtaacacc gctcgaggag     2460
ggcccgaaca aaaactcatc tcagaagaga tctgaatag cgccgtcgac catcatcatc     2520
atcatcattg aggtacccatc tagagtcgac ccgggcggcc tcgaggacgg ggtgaactac     2580
gcctgaggat ccgatctttt tccctctgcc aaaaattatg gggacatcat gaagcccctt     2640
gagcatctga cttctggcta ataaaggaaa tttatttca ttgcaatagt gtgttggaat     2700
tttttgtgtc tctcactcgg aagcaattcg ttgatctgaa tttcgaccac ccataatacc     2760
cattaccctg gtagataagt agcatggcgg gttaatcatt aactcaagg aaccccctagt     2820 gatggagttg gccactccct ctctgcgcgc tcgctcgctc actgaggccg gcgaccaaa     2880 ggtcgcccga cgcccgggct ttgcccgggc ggcctcagtg agcgagcgag cgcgcagcct     2940
taattaatta attaaggcct ta                                              2962
```

<210> SEQ ID NO 4
<211> LENGTH: 2947
<212> TYPE: DNA
<213> ORGANISM: Artificial Sequence
<220> FEATURE:
<223> OTHER INFORMATION: synthetically-generated vector

<400> SEQUENCE: 4

```
attaggctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc taccagggta     180
atggggatcc tctagaacta tagctagcat gcctgcaggc tgaccgccca acgacccccg     240
cccattgacg tcaataatga cgtatgttcc catagtaacg ccaataggga ctttccattg     300
acgtcaatgg gtggagtatt tacggtaaac tgcccacttg gcagtacatc aagtgtatca     360
tatgccaagt ccgcccccta ttgacgtcaa tgacggtaaa tggcccgcct ggcattatgc     420
ccagtacatg accttacggg actttcctac ttggcagtac atctacgtat tagtcatcgc     480
tattaccatg gtgatgcggt tttggcagta caccaatggg cgtggatagc ggtttgactc     540
acggggattt ccaagtctcc accccattga cgtcaatggg agtttgtttt ggcaccaaaa     600
tcaacgggac tttccaaaat gtcgtaataa ccccgccccg ttgacgcaaa tgggcggtag     660
gcgtgtacgg tgggaggtct atataagcag agctcgttta gtgaaccgtc agatcactag     720
aagctttatt gcggtagttt atcacagtta aattgctaac gcagtcagtg cttctgacac     780
aacagtctcg aacttaagct gcagaagttg gtcgtgaggc actgggcagg taagtatcaa     840
ggttacaaga caggtttaag gagaccaata gaaactgggc ttgtcgagac agagaagact     900
cttgcgtttc tgataggcac ctattggtct tactgacatc cactttgcct ttctctccac     960
aggtgtccac tcccagttca attacagctc ttaaggctag agtacttaat acgactcact    1020
ataggctagc ctcgagaatt cacgcgtggt acggtaccat ggggagcccc gcacatcggc    1080
ccgcgctgct gctgctgctg ccgcctctgc tgctgctgct gctgctgcgc gtcccgccca    1140
gccgcagctt cccaggatcg ggagactcac cactagaaga cgatgaagtc gggtattcac    1200
accctagata taaagatacc ccgtggtgct cccccatcaa ggtgaagtat ggggatgtgt    1260
actgcagggc ccctcaagga ggatactaca aaacagccct gggaaccagg tgcgacattc    1320
gctgccagaa gggctacgag ctgcatggct cttccctact gatctgccag tcaaacaaac    1380
gatggtctga caaggtcatc tgcaaacaaa agcgatgtcc tacccttgcc atgcagcaa     1440
atggagggtt taagtgtgta gatggtgcct actttaactc ccggtgtgag tattattgtt    1500
caccaggata cacgttgaaa ggggagcgga ccgtcacatg tatggacaac aaggcctgga    1560
gcggccggcc agcctcctgt gtggatatgg aacctcctag aatcaagtgc ccaagtgtga    1620
aggaacgcat tgcagaaccc aacaaactga cagtccgggt gtcctgggag acacccgaag    1680
gaagagacac agcagatgga attcttactg atgtcattct aaaaggcctc cccccaggct    1740
ccaactttcc agaaggagac cacaagatcc agtacacagt ctatgacaga gctgagaata    1800
agggcacttg caaatttcga gttaaagtaa gagtcaaacg ctgtggcaaa ctcaatgccc    1860
cagagaatgg ttacatgaag tgctcccagcg acggtgataa ttatggagcc acctgtgagt    1920
tctcctgcat cggcggctat gagctccagg gtagccctgc ccgagtatgt caatccaacc    1980
tggcttggtc tggcacggag cccacctgtg cagccatgaa cgtcaatgtg ggtgtcagaa    2040
cggcagctgc acttctggat cagttttatg agaaaaggag actcctcatt gtgtccacac    2100
```

```
ccacagcccg aaacctcctt taccggctcc agctaggaat gctgcagcaa gcacagtgtg    2160
gccttgatct tcgacacatc accgtggtgg agctggtggg tgtgttcccg actctcattg    2220
gcaggatagg agcaaagatt atgcctccag ccctagcgct gcagctcagg ctgttgctgc    2280
gaatcccact ctactccttc agtatggtgc tagtggataa gcatggcatg acaaagagc     2340
gctatgtctc cctggtgatg cctgtggccc tgttcaacct gattgacact tttcccttga    2400
gaaaagaaga gatggtccta caagccgaaa tgagccagac tgtaacaccc gaacaaaaac    2460
tcatctcaga gaggatctg  aatagcgccg tcgaccatca tcatcatcat cattgaggta    2520
ccctctagag tcgacccggg cggcctcgag gacggggtga actacgcctg aggatccgat    2580
cttttttccct ctgccaaaaa ttatggggac atcatgaagc cccttgagca tctgacttct    2640
ggctaataaa ggaaatttat tttcattgca atagtgtgtt ggaattttt  gtgtctctca    2700
ctcggaagca attcgttgat ctgaatttcg accacccata atacccatta ccctggtaga    2760
taagtagcat ggcgggttaa tcattaacta caaggaaccc ctagtgatgg agttggccac    2820
tccctctctg cgcgctcgct cgctcactga ggccgggcga ccaaaggtcg cccgacgccc    2880
gggcttttgcc cgggcggcct cagtgagcga gcgagcgcgc agccttaatt aattaattaa    2940
ggcctta                                                               2947
```

<210> SEQ ID NO 5
<211> LENGTH: 5752
<212> TYPE: DNA
<213> ORGANISM: Artificial Sequence
<220> FEATURE:
<223> OTHER INFORMATION: synthetically-generated plasmid

<400> SEQUENCE: 5

```
attaggctgc gcgctcgctc gctcactgag gccgcccggg caaagcccgg gcgtcgggcg      60
acctttggtc gcccggcctc agtgagcgag cgagcgcgca gagagggagt ggccaactcc    120
atcactaggg gttccttgta gttaatgatt aacccgccat gctacttatc taccagggta    180
atggggatcc tctagaacta tagctagcat gcctgcaggc tgaccgccca acgaccccccg    240
cccattgacg tcaataatga cgtatgttcc catagtaacg ccaatagggga ctttccattg    300
acgtcaatgg gtggagtatt tacggtaaac tgcccacttg gcagtacatc aagtgtatca    360
tatgccaagt ccgcccccta ttgacgtcaa tgacggtaaa tggcccgcct ggcattatgc    420
ccagtacatg accttacggg actttcctac ttggcagtac atctacgtat tagtcatcgc    480
tattaccatg gtgatgcggt tttggcagta caccaatggg cgtggatagc ggtttgactc    540
acggggattt ccaagtctcc accccattga cgtcaatggg agtttgtttt ggcaccaaaa    600
tcaacgggac tttccaaaat gtcgtaataa ccccgccccg ttgacgcaaa tgggcggtag    660
gcgtgtacgg tgggaggtct atataagcag agctcgttta gtgaaccgtc agatcactag    720
aagctttatt gcggtagttt atcacagtta aattgctaac gcagtcagtg cttctgacac    780
aacagtctcg aacttaagct gcagaagttg gtcgtgaggc actgggcagg taagtatcaa    840
ggttacaaga caggtttaag gagaccaata gaaactgggc ttgtcgagac agagaagact    900
cttgcgtttc tgataggcac ctattggtct tactgacatc cactttgcct ttctctccac    960
aggtgtccac tcccagttca attacagctc ttaaggctag agtacttaat acgactcact   1020
ataggctagc ctcgagaatt cacgcgtggt acggtaccat gatggagaca gacacactcc   1080
tgctatgggt actgctgctc tgggttccag gttccactgg tgacgcggcc cagccggcca   1140
```

```
ggcgcgcgcg ccgtacgaag cttgactcac cactagaaga cgatgaagtc gggtattcac    1200
accctagata taaagatacc ccgtggtgct cccccatcaa ggtgaagtat ggggatgtgt    1260
actgcagggc ccctcaagga ggatactaca aaacagccct gggaaccagg tgcgacattc    1320
gctgccagaa gggctacgag ctgcatggct cttccctact gatctgccag tcaaacaaac    1380
gatggtctga caaggtcatc tgcaaacaaa agcgatgtcc tacccttgcc atgccagcaa    1440
atggagggtt taagtgtgta gatggtgcct actttaactc ccggtgtgag tattattgtt    1500
caccaggata cacgttgaaa ggggagcgga ccgtcacatg tatggacaac aaggcctgga    1560
gcggccggcc agcctcctgt gtggatatgg aacctcctag aatcaagtgc ccaagtgtga    1620
aggaacgcat tgcagaaccc aacaaactga cagtccgggt gtcctgggag cacccgaag    1680 gaagagacac agcagatgga attcttactg atgtcattct aaaaggcctc cccccaggct    1740
ccaactttcc agaaggagac cacaagatcc agtacacagt ctatgacaga gctgagaata    1800
agggcacttg caaatttcga gttaaagtaa gagtcaaacg ctgtggcaaa ctcaatgccc    1860
cagagaatgg ttacatgaag tgctccagcg acggtgataa ttatggagcc acctgtgagt    1920
tctcctgcat cggcggctat gagctccagg gtagccctgc ccgagtatgt caatccaacc    1980
tggcttggtc tggcacggag cccacctgtg cagccatgaa cgtcaatgtg ggtgtcagaa    2040
cggcagctgc acttctggat cagttttatg agaaaaggag actcctcatt gtgtccacac    2100
ccacagcccg aaacctcctt taccggctcc agctaggaat gctgcagcaa gcacagtgtg    2160
gccttgatct tcgacacatc accgtggtgg agctggtggg tgtgttcccg actctcattg    2220
gcaggatagg agcaaagatt atgcctccag ccctagcgct gcagctcagg ctgttgctgc    2280
gaatcccact ctactccttc agtatggtgc tagtggataa gcatggcatg gacaaagagc    2340
gctatgtctc cctggtgatg cctgtggccc tgttcaacct gattgacact tttcccttga    2400
gaaaagaaga gatggtccta caagccgaaa tgagccagac ctgtaacacc gctcgaggag    2460
ggcccgaaca aaaactcatc tcagaagaga atctgaatag cgccgtcgac catcatcatc    2520
atcatcattg aggtaccctc tagagtcgac ccgggcggcc tcgaggacgg ggtgaactac    2580
gcctgaggat ccgatctttt tccctctgcc aaaaattatg gggacatcat gaagccccctt    2640 gagcatctga cttctggcta ataaaggaaa tttatttttca ttgcaatagt gtgttggaat    2700
tttttgtgtc tctcactcgg aagcaattcg ttgatctgaa tttcgaccac ccataatacc    2760
cattaccctg gtagataagt agcatggcgg gttaatcatt aactacaagg aacccctagt    2820
gatggagttg gccactccct ctctgcgcgc tcgctcgctc actgaggccg ggcgaccaaa    2880
ggtcgcccga cgcccgggct ttgcccgggc ggcctcagtg agcgagcgag cgcgcagcct    2940
taattaacct aattcactgg ccgtcgtttt acaacgtcgt gactgggaaa accctggcgt    3000
tacccaactt aatcgccttg cagcacatcc cctttcgcc agctggcgta atagcgaaga    3060
ggcccgcacc gatcgccctt cccaacagtt gcgcagcctg aatggcgaat gggacgcgcc    3120
ctgtagcggc gcattaagcg cggcgggtgt ggtggttacg cgcagcgtga ccgctacact    3180
tgccagcgcc ctagcgcccg ctcctttcgc tttcttccct cctttctcg ccacgttcgc    3240 cggctttccc cgtcaagctc taaatcgggg gctcccttta gggttccgat ttagtgcttt    3300
acggcacctc gaccccaaaa aacttgatta gggtgatggt tcacgtagtg gccatcgcc    3360 ctgatagacg gttttcgcc ctttgacgtt ggagtccacg ttctttaata gtggactctt    3420
gttccaaact ggaacaacac tcaacccttat ctcggtctat tcttttgatt tataagggat    3480
tttgccgatt tcggcctatt ggttaaaaaa tgagctgatt taacaaaaat ttaacgcgaa    3540
```

```
ttttaacaaa atattaacgc ttacaatttta ggtggcactt ttcgggggaaa tgtgcgcgga    3600
accccctattt gtttattttt ctaaatacat tcaaatatgt atccgctcat gagacaataa    3660
ccctgataaa tgcttcaata atattgaaaa aggaagagta tgagtattca acatttccgt    3720
gtcgccctta ttcccttttt tgcggcattt tgccttcctg tttttgctca cccagaaacg    3780
ctggtgaaag taaaagatgc tgaagatcag ttgggtgcac gagtgggtta catcgaactg    3840
gatctcaaca gcggtaagat ccttgagagt tttcgccccg aagaacgttt tccaatgatg    3900
agcacttttaa aagttctgct atgtggcgcg gtattatccc gtattgacgc cgggcaagag    3960
caactcggtc gccgcataca ctattctcag aatgacttgg ttgagtactc accagtcaca    4020
gaaaagcatc ttacggatgg catgacagta agagaattat gcagtgctgc cataaccatg    4080
agtgataaca ctgcggccaa cttacttctg acaacgatcg gaggaccgaa ggagctaacc    4140
gcttttttgc acaacatggg ggatcatgta actcgccttg atcgttggga accggagctg    4200
aatgaagcca taccaaacga cgagcgtgac accacgatgc ctgtagcaat ggcaacaacg    4260
ttgcgcaaac tattaactgg cgaactactt actctagctt cccggcaaca attaatagac    4320
tggatggagg cggataaagt tgcaggacca cttctgcgct cggcccttcc ggctggctgg    4380
tttattgctg ataaatctgg agccggtgag cgtgggtctc gcggtatcat tgcagcactg    4440
gggccagatg gtaagccctc ccgtatcgta gttatctaca cgacggggag tcaggcaact    4500
atggatgaac gaaatagaca gatcgctgag ataggtgcct cactgattaa gcattggtaa    4560
ctgtcagacc aagtttactc atatatactt tagattgatt taaaacttca ttttttaattt    4620
aaaaggatct aggtgaagat cctttttgat aatctcatga ccaaaatccc ttaacgtgag    4680
ttttcgttcc actgagcgtc agaccccgta gaaaagatca aaggatcttc ttgagatcct    4740
tttttttctgc gcgtaatctg ctgcttgcaa acaaaaaaac caccgctacc agcggtggtt    4800
tgtttgccgg atcaagagct accaactctt tttccgaagg taactggctt cagcagagcg    4860
cagataccaa atactgttct tctagtgtag ccgtagttag gccaccactt caagaactct    4920
gtagcaccgc ctacatacct cgctctgcta atcctgttac cagtggctgc tgccagtggc    4980
gataagtcgt gtcttaccgg gttggactca agacgatagt taccggataa ggcgcagcgg    5040
tcgggctgaa cggggggttc gtgcacacag cccagcttgg agcgaacgac ctacaccgaa    5100
ctgagatacc tacagcgtga gctatgagaa agcgccacgc ttcccgaagg gagaaaggcg    5160
gacaggtatc cggtaagcgg cagggtcgga acaggagagc gcacgaggga gcttccaggg    5220
ggaaacgcct ggtatcttta tagtcctgtc gggtttcgcc acctctgact tgagcgtcga    5280
tttttgtgat gctcgtcagg gggcggagc ctatggaaaa acgccagcaa cgcggccttt    5340
ttacggttcc tggccttttg ctggcctttt gctcacatgt tctttcctgc gttatcccct    5400
gattctgtgg ataaccgtat taccgccttt gagtgagctg ataccgctcg ccgcagccga    5460
acgaccgagc gcagcgagtc agtgagcgag gaagcggaag agcgcccaat acgcaaaccg    5520
cctctccccg cgcgttggcc gattcattaa tgcagctggc acgacaggtt cccgactgg    5580
aaagcgggca gtgagcgcaa cgcaattaat gtgagttagc tcactcatta ggcaccccag    5640
gctttacact ttatgcttcc ggctcgtatg ttgtgtggaa ttgtgagcgg ataacaattt    5700
cacacaggaa acagctatga ccatgattac gccagattta attaaggcct ta            5752
```

<210> SEQ ID NO 6
<211> LENGTH: 5737
<212> TYPE: DNA

<213> ORGANISM: Artificial Sequence
<220> FEATURE:
<223> OTHER INFORMATION: synthetically-generated plasmid

<400> SEQUENCE: 6

```
attaggctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc taccagggta     180
atggggatcc tctagaacta tagctagcat gcctgcaggc tgaccgccca acgaccccg      240
cccattgacg tcaataatga cgtatgttcc catagtaacg ccaatagggg ctttccattg     300
acgtcaatgg gtggagtatt tacggtaaac tgcccacttg gcagtacatc aagtgtatca     360
tatgccaagt ccgcccccta ttgacgtcaa tgacggtaaa tggcccgcct ggcattatgc     420
ccagtacatg accttacggg actttcctac ttggcagtac atctacgtat tagtcatcgc     480
tattaccatg gtgatgcggt tttggcagta caccaatggg cgtggatagc ggtttgactc     540
acggggattt ccaagtctcc accccattga cgtcaatggg agtttgtttt ggcaccaaaa     600
tcaacgggac tttccaaaat gtcgtaataa ccccgccccg ttgacgcaaa tgggcggtag     660
gcgtgtacgg tgggaggtct atataagcag agctcgttta gtgaaccgtc agatcactag     720
aagctttatt gcggtagttt atcacagtta aattgctaac gcagtcagtg cttctgacac     780
aacagtctcg aacttaagct gcagaagttg gtcgtgaggc actgggcagg taagtatcaa     840
ggttacaaga caggtttaag gagaccaata gaaactgggc ttgtcgagac agagaagact     900
cttgcgtttc tgataggcac ctattggtct tactgacatc cactttgcct ttctctccac     960
aggtgtccac tcccagttca attacagctc ttaaggctag agtacttaat acgactcact    1020
ataggctagc ctcgagaatt cacgcgtggt acggtaccat ggggagcccc gcacatcggc    1080
ccgcgctgct gctgctgctg ccgcctctgc tgctgctgct gctgctgcgc gtcccgccca    1140
gccgcagctt cccaggatcg ggagactcac cactagaaga cgatgaagtc gggtattcac    1200
accctagata taaagatacc ccgtggtgct cccccatcaa ggtgaagtat ggggatgtgt    1260
actgcagggc ccctcaagga ggatactaca aaacagccct gggaaccagg tgcgacattc    1320
gctgccagaa gggctacgag ctgcatggct cttccctact gatctgccag tcaaacaaac    1380
gatggtctga caaggtcatc tgcaaacaaa agcgatgtcc tacccttgcc atgcagcaa      1440
atggagggtt taagtgtgta gatggtgcct actttaactc ccggtgtgag tattattgtt    1500
caccaggata cacgttgaaa ggggagcgga ccgtcacatg tatggacaac aaggcctgga    1560
gcggccggcc agcctcctgt gtggatatgg aacctcctag aatcaagtgc ccaagtgtga    1620
aggaacgcat tgcagaaccc aacaaactga cagtccgggt gtcctgggag acacccgaag    1680
gaagagacac agcagatgga attcttactg atgtcattct aaaaggcctc cccccaggct    1740
ccaactttcc agaaggagac acaagatcc agtacacagt ctatgacaga gctgagaata    1800
agggcacttg caaatttcga gttaaagtaa gagtcaaacg ctgtgcaaa ctcaatgccc      1860
cagagaatgg ttacatgaag tgctccagcg acggtgataa ttatggagcc acctgtgagt    1920
tctcctgcat cggcggctat gagctccagg gtagccctgc ccgagtatgt caatccaacc    1980
tggcttggtc tggcacggag cccacctgtg cagccatgaa cgtcaatgtg ggtgtcagaa    2040
cggcagctgc acttctggat cagttttatg agaaaaggag actcctcatt gtgtccacac    2100
ccacagcccg aaacctcctt taccggctcc agctaggaat gctgcagcaa gcacagtgtg    2160
gccttgatct tcgacacatc accgtggtgg agctggtggg tgtgttcccg actctcattg    2220
```

```
gcaggatagg agcaaagatt atgcctccag ccctagcgct gcagctcagg ctgttgctgc    2280
gaatcccact ctactccttc agtatggtgc tagtggataa gcatggcatg gacaaagagc    2340
gctatgtctc cctggtgatg cctgtggccc tgttcaacct gattgacact tttcccttga    2400
gaaaagaaga gatggtccta caagccgaaa tgagccagac ctgtaacacc gaacaaaaac    2460
tcatctcaga gaggatctg aatagcgccg tcgaccatca tcatcatcat cattgaggta     2520
ccctctagag tcgacccggg cggcctcgag gacggggtga actacgcctg aggatccgat    2580 cttttttccct ctgccaaaaa ttatggggac atcatgaagc cccttgagca tctgacttct   2640
ggctaataaa ggaaatttat tttcattgca atagtgtgtt ggaattttt gtgtctctca     2700 ctcggaagca attcgttgat ctgaatttcg accacccata atacccatta ccctggtaga    2760
taagtagcat ggcgggttaa tcattaacta caaggaaccc ctagtgatgg agttggccac    2820
tccctctctg cgcgctcgct cgctcactga ggccgggcga ccaaaggtcg cccgacgccc    2880
gggctttgcc cggcggcct cagtgagcga gcgagcgcgc agccttaatt aacctaattc     2940
actggccgtc gttttacaac gtcgtgactg ggaaaaccct ggcgttaccc aacttaatcg    3000
ccttgcagca catccccctt cgccagctg gcgtaatagc gaagaggccc gcaccgatcg     3060
cccttcccaa cagttgcgca gcctgaatgg cgaatgggac gcgccctgta gcggcgcatt    3120
aagcgcggcg ggtgtggtgg ttacgcgcag cgtgaccgct acacttgcca gcgccctagc    3180
gcccgctcct ttcgctttct tcccttcctt tctcgccacg ttcgccggct ttccccgtca    3240
agctctaaat cggggctccc ctttaggt ccgatttagt gctttacggc acctcgaccc      3300
caaaaacttt gattagggtg atggttcacg tagtgggcca tcgccctgat agacggtttt    3360
tcgccctttg acgttggagt ccacgttctt taatagtgga ctcttgttcc aaactggaac    3420
aacactcaac cctatctcgg tctattcttt tgatttataa gggattttgc cgatttcggc    3480
ctattggtta aaaaatgagc tgatttaaca aaaatttaac gcgaatttta acaaaatatt    3540
aacgcttaca atttaggtgg cacttttcgg ggaaatgtgc gcggaacccc tatttgttta    3600
tttttctaaa tacattcaaa tatgtatccg ctcatgagac aataaccctg ataaatgctt    3660
caataatatt gaaaaggaa gagtatgagt attcaacatt tccgtgtcgc ccttattccc     3720
ttttttgcgg cattttgcct tcctgttttt gctcacccag aaacgctggt gaaagtaaaa    3780
gatgctgaag atcagttggg tgcacgagtg ggttacatcg aactggatct caacagcggt    3840
aagatccttg agagttttcg ccccgaagaa cgttttccaa tgatgagcac ttttaaagtt    3900
ctgctatgtg gcgcggtatt atcccgtatt gacgccgggc aagagcaact cggtcgccgc    3960
atacactatt ctcagaatga cttggttgag tactcaccag tcacagaaaa gcatcttacg    4020
gatggcatga cagtaagaga attatgcagt gctgccataa ccatgagtga taacactgcg    4080
gccaacttac ttctgacaac gatcggagga ccgaaggagc taaccgcttt tttgcacaac    4140 atggggatc atgtaactcg ccttgatcgt tgggaaccgg agctgaatga agccatacca    4200
aacgacgagc gtgacaccac gatgcctgta gcaatggcaa caacgttgcg caaactatta    4260
actggcgaac tacttactct agcttcccgg caacaattaa tagactggat ggaggcggat    4320
aaagttgcag gaccacttct gcgctcggcc cttccggctg gctggtttat tgctgataaa    4380
tctggagccg gtgagcgtgg gtctcgcggt atcattgcag cactggggcc agatggtaag    4440
ccctcccgta tcgtagttat ctacacgacg gggagtcagg caactatgga tgaacgaaat    4500
agacagatcg ctgagatagg tgcctcactg attaagcatt ggtaactgtc agaccaagtt    4560
```

-continued

```
tactcatata tactttagat tgatttaaaa cttcattttt aatttaaaag gatctaggtg    4620
aagatccttt ttgataatct catgaccaaa atcccttaac gtgagttttc gttccactga    4680
gcgtcagacc ccgtagaaaa gatcaaagga tcttcttgag atccttttt tctgcgcgta    4740 atctgctgct tgcaaacaaa aaaccaccg ctaccagcgg tggtttgttt gccggatcaa     4800
gagctaccaa ctcttttcc gaaggtaact ggcttcagca gagcgcagat accaaatact    4860
gttcttctag tgtagccgta gttaggccac cacttcaaga actctgtagc accgcctaca    4920
tacctcgctc tgctaatcct gttaccagtg gctgctgcca gtggcgataa gtcgtgtctt    4980
accgggttgg actcaagacg atagttaccg gataaggcgc agcggtcggg ctgaacgggg    5040
ggttcgtgca cacagcccag cttggagcga acgacctaca ccgaactgag atacctacag    5100
cgtgagctat gagaaagcgc cacgcttccc gaagggagaa aggcggacag gtatccggta    5160
agcggcaggg tcggaacagg agagcgcacg agggagcttc caggggaaa cgcctggtat     5220 ctttatagtc ctgtcgggtt tcgccacctc tgacttgagc gtcgatttt gtgatgctcg     5280 tcaggggggc ggagcctatg gaaaaacgcc agcaacgcgg cctttttacg gttcctggcc    5340
ttttgctggc cttttgctca catgttcttt cctgcgttat cccctgattc tgtggataac    5400
cgtattaccg cctttgagtg agctgatacc gctcgccgca gccgaacgac cgagcgcagc    5460
gagtcagtga gcgaggaagc ggaagagcgc ccaatacgca aaccgcctct ccccgcgcgt    5520
tggccgattc attaatgcag ctggcacgac aggtttcccg actggaaagc gggcagtgag    5580
cgcaacgcaa ttaatgtgag ttagctcact cattaggcac cccaggcttt acactttatg    5640
cttccggctc gtatgttgtg tggaattgtg agcggataac aatttcacac aggaaacagc    5700
tatgaccatg attacgccag atttaattaa ggcctta                             5737
```

<210> SEQ ID NO 7
<211> LENGTH: 405
<212> TYPE: PRT
<213> ORGANISM: Homo sapien

<400> SEQUENCE: 7

```
Met Gly Ser Pro Ala His Arg Pro Ala Leu Leu Leu Leu Pro Pro
1               5                   10                  15

Leu Leu Leu Leu Leu Leu Arg Val Pro Pro Ser Arg Ser Phe Pro
                20                  25                  30

Gly Ser Gly Asp Ser Pro Leu Glu Asp Asp Val Gly Tyr Ser His
                35                  40                  45

Pro Arg Tyr Lys Asp Thr Pro Trp Cys Ser Pro Ile Lys Val Lys Tyr
50                  55                  60

Gly Asp Val Tyr Cys Arg Ala Pro Gln Gly Gly Tyr Tyr Lys Thr Ala
65                  70                  75                  80

Leu Gly Thr Arg Cys Asp Ile Arg Cys Gln Lys Gly Tyr Glu Leu His
                85                  90                  95

Gly Ser Ser Leu Leu Ile Cys Gln Ser Asn Lys Arg Trp Ser Asp Lys
                100                 105                 110

Val Ile Cys Lys His Met Glu Pro Pro Arg Ile Lys Cys Pro Ser Val
                115                 120                 125

Lys Glu Arg Ile Ala Glu Pro Asn Lys Leu Thr Val Arg Val Ser Trp
                130                 135                 140

Glu Thr Pro Glu Gly Arg Asp Thr Ala Asp Gly Ile Leu Thr Asp Val
145                 150                 155                 160

Ile Leu Lys Gly Leu Pro Pro Gly Ser Asn Phe Pro Glu Gly Asp His
```

165                 170                 175
Lys Ile Gln Tyr Thr Val Tyr Asp Arg Ala Glu Asn Lys Gly Thr Cys
                180                 185                 190

Lys Phe Arg Val Lys Val Arg Val Lys Arg Cys Gly Lys Leu Asn Ala
                195                 200                 205

Pro Glu Asn Gly Tyr Met Lys Cys Ser Ser Asp Gly Asp Asn Tyr Gly
            210                 215                 220

Ala Thr Cys Glu Phe Ser Cys Ile Gly Gly Tyr Glu Leu Gln Gly Ser
225                 230                 235                 240

Pro Ala Arg Val Cys Gln Ser Asn Leu Ala Trp Ser Gly Thr Glu Pro
                245                 250                 255

Thr Cys Ala Ala Met Asn Val Asn Val Gly Val Arg Thr Ala Ala Ala
                260                 265                 270

Leu Leu Asp Gln Phe Tyr Glu Lys Arg Leu Leu Ile Val Ser Thr
                275                 280                 285

Pro Thr Ala Arg Asn Leu Leu Tyr Arg Leu Gln Leu Gly Met Leu Gln
            290                 295                 300

Gln Ala Gln Cys Gly Leu Asp Leu Arg His Ile Thr Val Val Glu Leu
305                 310                 315                 320

Val Gly Val Phe Pro Thr Leu Ile Gly Arg Ile Gly Ala Lys Ile Met
                325                 330                 335

Pro Pro Ala Leu Ala Leu Gln Leu Arg Leu Leu Arg Ile Pro Leu
            340                 345                 350

Tyr Ser Phe Ser Met Val Leu Val Asp Lys His Gly Met Asp Lys Glu
                355                 360                 365

Arg Tyr Val Ser Leu Val Met Pro Val Ala Leu Phe Asn Leu Ile Asp
            370                 375                 380

Thr Phe Pro Leu Arg Lys Glu Glu Met Val Leu Gln Ala Glu Met Ser
385                 390                 395                 400

Gln Thr Cys Asn Thr
                405

<210> SEQ ID NO 8
<211> LENGTH: 379
<212> TYPE: PRT
<213> ORGANISM: Homo sapien

<400> SEQUENCE: 8

Met Gly Ser Pro Ala His Arg Pro Ala Leu Leu Leu Leu Pro Pro
1               5                   10                  15

Leu Leu Leu Leu Leu Leu Leu Arg Val Pro Pro Ser Arg Ser Phe Pro
                20                  25                  30

Gly Ser Gly Asp Ser Pro Leu Glu Asp Asp Glu Val Gly Tyr Ser His
            35                  40                  45

Pro Arg Tyr Lys Asp Thr Pro Trp Cys Ser Pro Ile Lys Val Lys Tyr
        50                  55                  60

Gly Asp Val Tyr Cys Arg Ala Pro Gln Gly Gly Tyr Tyr Lys Thr Ala
65                  70                  75                  80

Leu Gly Thr Arg Cys Asp Ile Arg Cys Gln Lys Gly Tyr Glu Leu His
                85                  90                  95

Gly Ser Ser Leu Leu Ile Cys Gln Ser Asn Lys Arg Trp Ser Asp Lys
            100                 105                 110

Val Ile Cys Lys Gln Lys Arg Cys Pro Thr Leu Ala Met Pro Ala Asn
        115                 120                 125

-continued

```
Gly Gly Phe Lys Cys Val Asp Gly Ala Tyr Phe Asn Ser Arg Cys Glu
        130                 135                 140
Tyr Tyr Cys Ser Pro Gly Tyr Thr Leu Lys Gly Glu Arg Thr Val Thr
145                 150                 155                 160
Cys Met Asp Asn Lys Ala Trp Ser Gly Arg Pro Ala Ser Cys Val Asp
                165                 170                 175
Met Glu Pro Pro Arg Ile Lys Cys Pro Ser Val Lys Glu Arg Ile Ala
            180                 185                 190
Glu Pro Asn Lys Leu Thr Val Arg Val Ser Trp Glu Thr Pro Glu Gly
        195                 200                 205
Arg Asp Thr Ala Asp Gly Ile Leu Thr Asp Val Ile Leu Lys Gly Leu
    210                 215                 220
Pro Pro Gly Ser Asn Phe Pro Glu Gly Asp His Lys Ile Gln Tyr Thr
225                 230                 235                 240
Val Tyr Asp Arg Ala Glu Asn Lys Gly Thr Cys Lys Phe Arg Val Lys
                245                 250                 255
Val Arg Val Lys Arg Cys Gly Lys Leu Asn Ala Pro Glu Asn Gly Tyr
            260                 265                 270
Met Lys Cys Ser Ser Asp Gly Asp Asn Tyr Gly Ala Thr Cys Glu Phe
        275                 280                 285
Ser Cys Ile Gly Gly Tyr Glu Leu Gln Gly Ser Pro Ala Arg Val Cys
    290                 295                 300
Gln Ser Asn Leu Ala Trp Ser Gly Thr Glu Pro Thr Cys Ala Ala Met
305                 310                 315                 320
Asn Val Asn Val Gly Val Arg Thr Ala Ala Ala Leu Leu Asp Gln Phe
                325                 330                 335
Tyr Glu Lys Arg Arg Leu Leu Ile Val Ser Thr Pro Thr Ala Arg Asn
            340                 345                 350
Leu Leu Tyr Arg Leu Gln Leu Gly Met Leu Gln Ala Val Ala Ala Asn
        355                 360                 365
Pro Thr Leu Leu Leu Gln Tyr Gly Ala Ser Gly
370                 375
```

SRPX FOR TREATMENT OF CANCER

CROSS-REFERENCE TO RELATED APPLICATIONS

This application is continuation application of U.S. application Ser. No. 15/985,922, filed May 22, 2018, now U.S. Pat. No. 10,624,951, which is a continuation application of U.S. application Ser. No. 15/074,714, filed Mar. 18, 2016, now U.S. Pat. No. 10,130,679, which is a continuation application of U.S. application Ser. No. 14/240,813, filed on Feb. 25, 2014, now U.S. Pat. No. 9,290,744, which is a national phase application under 35 U.S.C. § 371 of PCT International Application No. PCT/US2012/055641, filed Sep. 14, 2012, which claims the benefit under 35 USC § 119(e) of U.S. Provisional Application Ser. No. 61/534,655, filed Sep. 14, 2011. The entire contents of each of the foregoing applications is hereby incorporated by reference.

TECHNICAL FIELD

This invention relates to treatment of cancers with agents that include a polypeptide.

BACKGROUND

Lung cancer, the leading cause of cancer-related death worldwide, will account for an estimated 157,000 deaths in the United States this year. Approximately 85 to 90% of all cases of lung cancer are non-small-cell lung cancer (NSCLC). There are three main forms of NSCLC, which are classified according to histological subtype: adenocarcinoma (accounting for 40% of lung cancers), squamous cell carcinoma (25%) and large-cell carcinomas (10%). Advanced-stage NSCLC is currently considered an incurable disease for which standard chemotherapy provides marginal improvement in overall survival at the expense of substantial morbidity and mortality. Furthermore, fewer than 30% of patients with metastatic NSCLC have a response to platinum-based chemotherapy, the most commonly used initial treatment in this stage of the disease. Although newer chemotherapeutic agents, such as bevacizumab, have been introduced, the median overall survival of patients with metastatic NSCLC remains approximately 1 year (Sandler et al., 2006, N. Engl. J. Med., 355:2542; Schiller et al., 2002, N. Engl. J. Med., 346:92), and only 3 to 4% of patients with metastatic NSCLC survive 5 years after diagnosis.

SUMMARY

This disclosure is based, in part, on the surprising discovery that, although previously believed to be active intracellularly (see, e.g., Tambe et al., Tambe et al. 2007, Carcinogenesis 28(4):777-784, especially FIG. 4B, which suggests that SRPX is localized to the endoplasmic reticulum), a secreted form of the Sushi-Repeat-containing Protein, X-linked (SRPX) protein induces senescence and/or apoptosis in cancer cells. Described herein are methods of diagnosing and treating tumors (e.g., cancers), inducing cellular apoptosis, inducing cellular senescence, and inhibiting cellular proliferation using SRPX agents, e.g., agents comprising SRPX polypeptides delivered to the extracellular surface of tumor cells, or comprising cells (e.g., autologous cells) expressing and secreting exogenous SRPX polypeptides and implanted into or near the tumor.

In one aspect, this application features methods of treating a tumor in a subject by identifying a subject having, at risk for, or suspected of having a tumor; and administering to the extracellular surface of tumor cells in the subject an effective amount of an SRPX agent, e.g., polypeptide or active fragment thereof, thereby treating the tumor. In some embodiments, the tumor is a cancer (e.g., a lung cancer (e.g., a non-small cell lung carcinoma, small-cell carcinoma, adenocarcinoma, or squamous cell carcinoma), a melanoma, carcinoma, breast cancer, ovarian cancer, pancreatic cancer, colorectal carcinoma, or papillary thyroid carcinoma). In some embodiments, the tumor comprises cells in which expression of SRPX is significantly reduced, e.g., undetectable, as compared to wild-type (normal) cells of the same tissue. In some embodiments, the methods include identifying a subject as having a tumor in which expression of SRPX is significantly reduced, e.g., by detecting expression of SRPX in a sample comprising cells from the tumor.

In another aspect, this application features methods of inducing senescence in a cell (e.g., a tumor cell or cancer cell) that include administering to the extracellular surface of the cell an effective amount of a SRPX agent, e.g., polypeptide or active fragment thereof. In some embodiments, the cell is a tumor cell.

In a further aspect, this application features methods of inducing apoptosis in a cell (e.g., a tumor cell or cancer cell) that include administering to the extracellular surface of the cell an effective amount of a SRPX agent, e.g., polypeptide or active fragment thereof.

In another aspect, this application features methods of inhibiting proliferation of a cell (e.g., a tumor cell or cancer cell) that include administering to the extracellular surface of the cell an effective amount of a SRPX agent, e.g., polypeptide or active fragment thereof.

In a further aspect, this application features methods of inhibiting growth (e.g., metastatic growth) in a subject of a tumor that include administering to the extracellular surface of cells of the tumor in the subject an effective amount of a SRPX agent, e.g., polypeptide or active fragment thereof.

In some embodiments, expression of SRPX is significantly reduced, e.g., undetectable, in the cell as compared to a wild-type (normal) cell of the same type/tissue type. In some embodiments, the methods include identifying a cell in which expression of SRPX is significantly reduced, e.g., by detecting expression of SRPX in a sample comprising cells from a tumor.

In another aspect, this application features the use of a SRPX agent in the preparation of a medicament for the treatment of a tumor or cancer (e.g., a lung cancer (e.g., a non-small cell lung carcinoma, small-cell carcinoma, adenocarcinoma, or squamous cell carcinoma), a melanoma, carcinoma, breast cancer, ovarian cancer, pancreatic cancer, colorectal carcinoma, or papillary thyroid carcinoma) in a subject. Compositions comprising a SRPX polypeptide or active fragment thereof are suitable for administration to the extracellular surface of cells in the tumor. In some embodiments, the tumor or cancer is metastatic.

In a further aspect, this application features an isolated SRPX agent for treating a tumor or cancer (e.g., a lung cancer (e.g., a non-small cell lung carcinoma, small-cell carcinoma, adenocarcinoma, or squamous cell carcinoma), a melanoma, carcinoma, breast cancer, ovarian cancer, pancreatic cancer, colorectal carcinoma, or papillary thyroid carcinoma) in a subject. Compositions comprising a SRPX polypeptide or active fragment thereof are suitable for administration to the extracellular surface of cells in the tumor. In some embodiments, the tumor or cancer is metastatic.

In some embodiments, the tumor comprises cells in which expression of SRPX is significantly reduced, e.g., undetectable, as compared to wild-type (normal) cells of the same tissue. In some embodiments, the methods include identifying a subject as having a tumor in which expression of SRPX is significantly reduced, e.g., by detecting expression of SRPX in a sample comprising cells from the tumor.

In some embodiments, the SRPX agent is a composition that includes a polypeptide having a sequence at least 80% identical (e.g., at least 85%, 90%, 95%, 98%, or 99% identical) to SEQ ID NO:1 or SEQ ID NO:2, or an active fragment of either. The polypeptide can be conjugated to a heterologous moiety (e.g., a heterologous polypeptide sequence). In some embodiments, the SRPX agent includes a functional fragment or domain of SEQ ID NO:1 or SEQ ID NO:2, or a fragment of either. The SRPX agent can be administered, e.g., topically, systemically, or locally (e.g., by a drug-releasing implant). The SRPX polypeptide is administered to the extracellular surface of cells in the tumor.

In some embodiments, the SRPX agent is administered by introducing into the subject a composition that induces the expression of SRPX or an active fragment or analog thereof, e.g., a nucleic acid encoding a polypeptide that includes a sequence at least 80% identical (e.g., at least 85%, 90%, 95%, 98%, or 99% identical) to SEQ ID NO:1 or SEQ ID NO:2, or a fragment of either. The nucleic acid can be in a vector, e.g., a viral vector (e.g., an adenovirus vector, an adeno-associated virus vector, a retrovirus vector, or a lentivirus vector). In some embodiments, the SRPX agent is administered by introducing into the subject a cell that includes a nucleic acid encoding a polypeptide that includes a sequence at least 80% identical (e.g., at least 85%, 90%, 95%, 98%, or 99% identical) to SEQ ID NO:1 or SEQ ID NO:2, or a fragment of either, and wherein the cell secretes the polypeptide.

In another aspect, the invention features methods for treating a tumor in a subject. The methods include identifying a subject having, at risk for, or suspected of having a tumor; and administering to the subject an effective amount of a population of cells expressing a nucleic acid encoding a polypeptide that is at least 95% identical to SEQ ID NO:1, wherein the cells are administered into or near the tumor, thereby treating the tumor.

An active or functional fragment is a portion of the SRPX protein that retains the ability to induce cancer cell senescence and/or apoptosis, e.g., is able to induce cancer cell death or senescence (e.g., lung cancer cell death or senescence) in a relevant assay known in the art, e.g., an assay described herein.

"Polypeptide" and "protein" are used interchangeably and mean any peptide-linked chain of amino acids, regardless of length or post-translational modification.

As used herein, a subject "at risk of developing cancer" is a subject that has a predisposition to develop cancer, i.e., a genetic or familial predisposition to develop cancer or has been exposed to conditions that can result in cancer. From the above it will be clear that subjects "at risk of developing cancer" are not all subjects.

A subject "suspected of having cancer" is one having one or more symptoms of cancer. Symptoms of cancer are well-known to those of skill in the art and include, without limitation, weight loss, weakness, excessive fatigue, difficulty eating, loss of appetite, unusual mole features, newly pigmented skin area, skin growths, skin ulcers, skin lumps, chronic cough, worsening breathlessness, breathing difficulty, enlarged lymph nodes, coughing up blood, blood in the urine, blood in stool, nausea, vomiting, liver metastases, lung metastases, bone metastases, breast or nipple changes, nipple discharge, abdominal fullness, bloating, fluid in peritoneal cavity, constipation, abdominal distension, perforation of colon, acute peritonitis (infection, fever, pain), vaginal bleeding, pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, pancreas metastases, difficulty swallowing, and the like. For example, a patient who has been diagnosed by a physician as having cancer is still suspected of having cancer.

The term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. In some embodiments, the present methods can be used to treat a subject having an epithelial cancer, e.g., a solid tumor of epithelial origin, e.g., lung, breast, ovarian, prostate, renal, pancreatic, or colon cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4C-4D depict the sequence of plasmid pAAVCMVPI.SRPXsec (SEQ ID NO:5), which includes an adeno associated vector (AAV) expressing the polypeptide of SEQ ID NO:1 with a heterologous signal sequence and C-terminal Myc and His$_6$ tags.

FIGS. 5C-5D depict the sequence of plasmid pAAVCMVPI.SRPXwt (SEQ ID NO:6), which includes an AAV expressing the polypeptide of SEQ ID NO:2 with C-terminal Myc and His$_6$ tags.

DETAILED DESCRIPTION

Figure 1A:
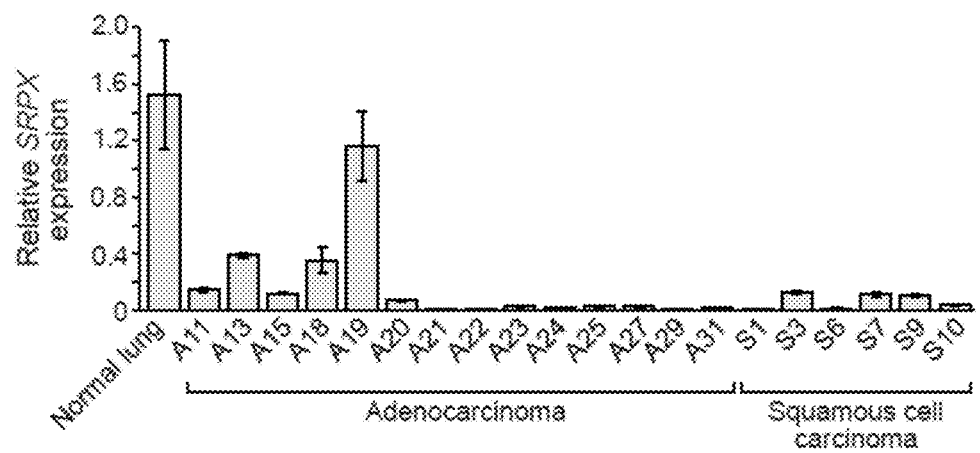
FIG. 1A is a bar graph depicting relative SRPX expression in normal lung tissue and tumor samples from patients with lung adenocarcinomas and squamous cell carcinomas.

This disclosure includes methods of treating tumors (e.g., cancers), inducing cellular apoptosis, inducing cellular senescence, and inhibiting cellular proliferation with SRPX agents.

SRPX Agents

SRPX agents that can be used with the methods described herein are agents that include an SRPX polypeptide sequence and, alternatively, one or more polypeptide or non-polypeptide moieties, such that the agent has at least 25% (e.g., at least: 30%; 40%; 50%; 60%; 70%; 75%; 80%; 85%; 90%; 95%; 97%; 98%; 99%; 99.5%, or 100% or even greater) of the ability of rSRPX (see Example 1) to inhibit the proliferation of one or more of NCI-H23, EKVX, HOP-62, HOP-92, HCT-15, SW-620, COL0205, HT29, HCT-116, KM-12, CCRF-CEM, K-562, MOLT-4, SR, RPMI-8226, A549-ATCC, NCI-H226, NCI-H322M in vitro. Exemplary agents include fragments and analogs of SRPX (see below). The SRPX polypeptide sequence can include a mature, soluble SRPX polypeptide (e.g., SEQ ID NO:1 or residues 29, 30, 31, 32, 33, 34 or 35 to 464 of SEQ ID NO:2), one or more domains of SRPX, or fragments or variants thereof. Exemplary fragments of SRPX include residues 59 to 115, 59 to 175, 59 to 254, 59 to 317, 120 to 175, 120 to 254, 120 to 317, 175 to 254, 175 to 317, and 262 to 317 of SEQ ID NO:2. An exemplary mature, soluble SRPX polypeptide is provided as:

(SEQ ID NO: 1)
DSPLEDDEVGYSHPRYKDTPWCSPIKVKYGDVYCRAPQGGYYKTALGTR

CDIRCQKGYELHGSSLLICQSNKRWSDKVICKQKRCPTLAMPANGGFKC

VDGAYFNSRCEYYCSPGYTLKGERTVTCMDNKAWSGRPASCVDMEPPRI

KCPSVKERIAEPNKLTVRVSWETPEGRDTADGILTDVILKGLPPGSNFP

EGDHKIQYTVYDRAENKGTCKFRVKVRVKRCGKLNAPENGYMKCSSDGD

NYGATCEFSCIGGYELQGSPARVCQSNLAWSGTEPTCAAMNVNVGVRTA

AALLDQFYEKRRLLIVSTPTARNLLYRLQLGMLQQAQCGLDLRHITVVE

LVGVFPTLIGRIGAKIMPPALALQLRLLLRIPLYSFSMVLVDKHGMDKE

RYVSLVMPVALFNLIDTFPLRKEEMVLQAEMSQTCNT

In certain embodiments, SRPX polypeptides include sequences substantially identical to all or a portion of a naturally occurring SRPX polypeptide. Polypeptides "substantially identical" to the SRPX polypeptide sequence described herein can contain an amino acid sequence that is at least 65% (e.g., at least 75%, 80%, 85%, 90%, 95%, 98%, or 99%, e.g., 100%), identical to the amino acid sequences of the SRPX polypeptide represented by SEQ ID NO:1, an amino acid sequence of GenBank Accession No. NP_006298.1 (SEQ ID NO:2), NP_001164221.1 (residues 1 to 32 and 53 to 464 of SEQ ID NO:2), NP_001164222.1 (SEQ ID NO:7), or NP_001164223.1 (SEQ ID NO:8), or a fragment as disclosed herein (e.g., residues 29, 30, 31, 32, 33, 34, 35, or 36 to 464 of SEQ ID NO:2 or residues 59 to 115, 59 to 175, 59 to 254, 59 to 317, 120 to 175, 120 to 254, 120 to 317, 175 to 254, 175 to 317, and 262 to 317 of SEQ ID NO:2). The human NP_006298.1 sequence is shown below.

(SEQ ID NO: 2)
MGSPAHRPALLLLLPPLLLLLLLRVPPSRSFPGSGDSPLEDDEVGYSHP

RYKDTPWCSPIKVKYGDVYCRAPQGGYYKTALGTRCDIRCQKGYELHGS

SLLICQSNKRWSDKVICKQKRCPTLAMPANGGFKCVDGAYFNSRCEYYC

SPGYTLKGERTVTCMDNKAWSGRPASCVDMEPPRIKCPSVKERIAEPNK

LTVRVSWETPEGRDTADGILTDVILKGLPPGSNFPEGDHKIQYTVYDRA

ENKGTCKFRVKVRVKRCGKLNAPENGYMKCSSDGDNYGATCEFSCIGGY

ELQGSPARVCQSNLAWSGTEPTCAAMNVNVGVRTAAALLDQFYEKRRLL

IVSTPTARNLLYRLQLGMLQQAQCGLDLRHITVVELVGVFPTLIGRIGA

KIMPPALALQLRLLLRIPLYSFSMVLVDKHGMDKERYVSLVMPVALFNL

IDTFPLRKEEMVLQAEMSQTCNT

The human NP_001164222.1 sequence is shown below.

(SEQ ID NO: 7)
MGSPAHRPALLLLLPPLLLLLLLRVPPSRSFPGSGDSPLEDDEVGYSHP

RYKDTPWCSPIKVKYGDVYCRAPQGGYYKTALGTRCDIRCQKGYELHGS

SLLICQSNKRWSDKVICKHMEPPRIKCPSVKERIAEPNKLTVRVSWETP

EGRDTADGILTDVILKGLPPGSNFPEGDHKIQYTVYDRAENKGTCKFRV

KVRVKRCGKLNAPENGYMKCSSDGDNYGATCEFSCIGGYELQGSPARVC

QSNLAWSGTEPTCAAMNVNVGVRTAAALLDQFYEKRRLLIVSTPTARNL

-continued

LYRLQLGMLQQAQCGLDLRHITVVELVGVFPTLIGRIGAKIMPPALALQ

LRLLLRIPLYSFSMVLVDKHGMDKERYVSLVMPVALFNLIDTFPLRKEE

MVLQAEMSQTCNT

The human NP_001164223.1 sequence is shown below.

(SEQ ID NO: 8)
MGSPAHRPALLLLLPPLLLLLLLRVPPSRSFPGSGDSPLEDDEVGYSHP

RYKDTPWCSPIKVKYGDVYCRAPQGGYYKTALGTRCDIRCQKGYELHGS

SLLICQSNKRWSDKVICKQKRCPTLAMPANGGFKCVDGAYFNSRCEYYC

SPGYTLKGERTVTCMDNKAWSGRPASCVDMEPPRIKCPSVKERIAEPNK

LTVRVSWETPEGRDTADGILTDVILKGLPPGSNFPEGDHKIQYTVYDRA

ENKGTCKFRVKVRVKRCGKLNAPENGYMKCSSDGDNYGATCEFSCIGGY

ELQGSPARVCQSNLAWSGTEPTCAAMNVNVGVRTAAALLDQFYEKRRLL

IVSTPTARNLLYRLQLGMLQAVAANPTLLLQYGASG

Any of the above polypeptides can be provided in mature form without the signal sequence (e.g., residues 1 to 29, 30, 31, 32, 33, 34, or 35 of SEQ ID NO: 2, 7, or 8).

Furthermore, a SRPX polypeptide (e.g., SEQ ID NO:1, an amino acid sequence of GenBank Accession No. NP_006298.1 (SEQ ID NO:2), NP_001164221.1, NP_001164222.1, or NP_006298.1, or a fragment as disclosed herein (e.g., residues 29, 30, 31, 32, 33, 34 or 35 to 464 of SEQ ID NO:2 or residues 59 to 115, 59 to 175, 59 to 254, 59 to 317, 120 to 175, 120 to 254, 120 to 317, 175 to 254, 175 to 317, and 262 to 317 of SEQ ID NO:2)) with up to 50, e.g., 1, 3, 5, 10, 15, 20, 25, 30, or 40, amino acid insertions, deletions, or substitutions (e.g., conservative amino acid substitutions) will be useful in the compositions and methods described herein. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The percent identity between two amino acid sequences can be determined using the BLAST 2.0 program, which is available to the public at ncbi.nlm.nih.gov/BLAST. Sequence comparison is performed using the default parameters (BLOSUM 62 matrix, gap existence cost of 11, per residue gap cost of 1, and a lambda ratio of 0.85). The mathematical algorithm used in BLAST programs is described in Altschul et al., 1997, Nucleic Acids Research, 25:3389-3402.

SRPX polypeptides useful in the methods described herein can be, but are not limited to, recombinant polypeptides and naturally occurring polypeptides. A SRPX polypeptide can be obtained from any human or mammalian species, and include alternatively spliced forms and other isoforms that have the disclosed activities. Non-human SRPX polypeptides with similarity to human SRPX polypeptides have been identified in chimpanzees (e.g., GenBank Accession No. XP_521003.3), rhesus monkeys (e.g., GenBank Accession Nos. XP_001083979.1, XP_001084091.1), common marmosets (e.g., GenBank Accession Nos. XP_002762821.1, XP_002762820.1), Sumatran orangutans (GenBank Accession Nos. XP_002831567.1, XP_002831566.1), white-cheeked gibbons (GenBank Accession No. XP_003271118.1), cattle (e.g., GenBank Accession Nos. DAA12706.1, NP_001035579.1), horses (e.g., GenBank Accession No. XP_001489693.3), dogs (e.g., GenBank Accession No. XP_548948.3), mice (e.g., GenBank Accession Nos. CAM18748.1, NP_058607.1), and rats (e.g., GenBank Accession Nos. AAH87639.1, NP_071969.1).

Also useful in the new methods are fusion proteins in which a portion of a SRPX polypeptide is fused to an unrelated polypeptide (e.g., a marker polypeptide or purification tag) to create a fusion protein. For example, the polypeptide can be fused to a peptide tag to facilitate purification (e.g., a hexa-histidine tag or a FLAG tag to facilitate purification of bacterially expressed polypeptides or to a hemagglutinin tag or a FLAG tag to facilitate purification of polypeptides expressed in eukaryotic cells). Also useful are, for example, polypeptides that include a first portion and a second portion; the first portion includes, e.g., a SRPX polypeptide, and the second portion includes, e.g., a detectable marker or a serum protein, e.g., an immunoglobulin constant region, or human serum albumin.

SRPX contains three complement control protein (CCP) modules (aka short consensus repeats (SCRs) or SUSHI repeats; Norman et al., J. Mol. Biol., 219:717-725; Kirkitadze et al., 2001, Immunol. Rev., 180:146-161) at residues 59 to 115, 120 to 175, and 262 to 317 of SEQ ID NO:2. Additionally, the protein contains a hyaline repeat (HYR) domain at residues 175 to 254 of SEQ ID NO:2. Exemplary fragments of SRPX can include one or more of residues 59 to 115, 59 to 175, 59 to 254, 59 to 317, 120 to 175, 120 to 254, 120 to 317, 175 to 254, 175 to 317, or 262 to 317 of SEQ ID NO:2. Conserved residues and domains can be used when producing fragments, analogs, and variants of SRPX polypeptides.

A SRPX agent can have one or more chemical modifications (e.g., posttranslational modifications) at one or more sites on the polypeptide, e.g., at the amino or carboxy terminus. Methods of chemical modification are well-known to those of skill in the art, and can be used to alter one or more properties, e.g., activity, stability, retention, or pharmacokinetics of the SRPX agent. Exemplary modifications include glycosylation and PEGylation. SRPX contains a putative 0-glycosylation site at residue 383 of SEQ ID NO:2. Pegylation of proteins is described in US 2006/0100144. Similar modifications and methods can be used with SRPX agents.

A SRPX agent can also be a peptidomimetic version of a SRPX polypeptide (e.g., SEQ ID NO:1), functional fragment, or variant thereof. These polypeptides can be modified according to the methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., *J. Biol. Chem.*, 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β³-amino acids"), phosphorous analogs of amino acids, such as amino phosphonic acids and amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules.

Also useful in the methods disclosed herein are nucleic acid molecules that encode SRPX agents described herein, e.g., naturally occurring SRPX polypeptides or forms of SRPX polypeptides in which naturally occurring amino acid sequences are altered or deleted (e.g., fragments or analogs of SRPX). Certain nucleic acids can encode polypeptides that are soluble under normal physiological conditions. SRPX agents can be expressed (e.g., exogenously expressed) within a cell by any means known in the art. To generate cells that express SRPX agents, the cells can be transfected, transformed, or transduced using any of a variety of techniques known in the art. Any number of transfection, transformation, and transduction protocols known to those in the art may be used, for example those outlined in Current Protocols in Molecular Biology, John Wiley & Sons, New York, N.Y., or in numerous kits available commercially (e.g., Invitrogen Life Technologies, Carlsbad, Calif.). Such techniques may result in stable or transient transformants. One suitable transfection technique is electroporation, which can be performed on a variety of cell types, including mammalian cells, yeast cells and bacteria, using commercially available equipment. Optimal conditions for electroporation (including voltage, resistance and pulse length) are experimentally determined for the particular host cell type, and general guidelines for optimizing electroporation can be obtained from manufacturers.

When the polypeptide expressed by a nucleic acid is intended to be secreted, the nucleic acid sequence can encode an N-terminal signal sequence that directs secretion of the polypeptide. In some embodiments, the signal sequence is a heterologous signal sequence. Signal sequences that function in prokaryotes and eukaryotes are well known, and one of ordinary skill can select or design an appropriate signal sequence accordingly. In some embodiments, the nucleic acid can encode a SRPX polypeptide, variant, or fragment as disclosed herein with a SRPX or heterologous signal sequence.

Exemplary methods of administering SRPX agents include introducing into a subject a nucleic acid that encodes an SRPX agent described herein. In some embodiments, the nucleic acid that encodes the SRPX agent is contained within a vector, e.g., as a virus that includes a nucleic acid that expresses the SRPX agent. Exemplary viral vectors include adenoviruses (reviewed in Altaras et al., 2005, Adv. Biochem. Eng. Biotechnol., 99:193-260), adeno-associated viruses (reviewed in Park et al., 2008, Front. Biosci., 13:2653-59; see also Williams, 2007, Mol. Ther., 15:2053-54), parvoviruses, lentiviruses, retroviruses (reviewed in Tai et al., 2008, Front. Biosci., 13:3083-95), and the herpes simplex virus. Methods of delivery of nucleic acids are reviewed in Patil et al., 2005, AAPS J., 7:E61-77, which is incorporated herein by reference in its entirety.

Figure 4A:
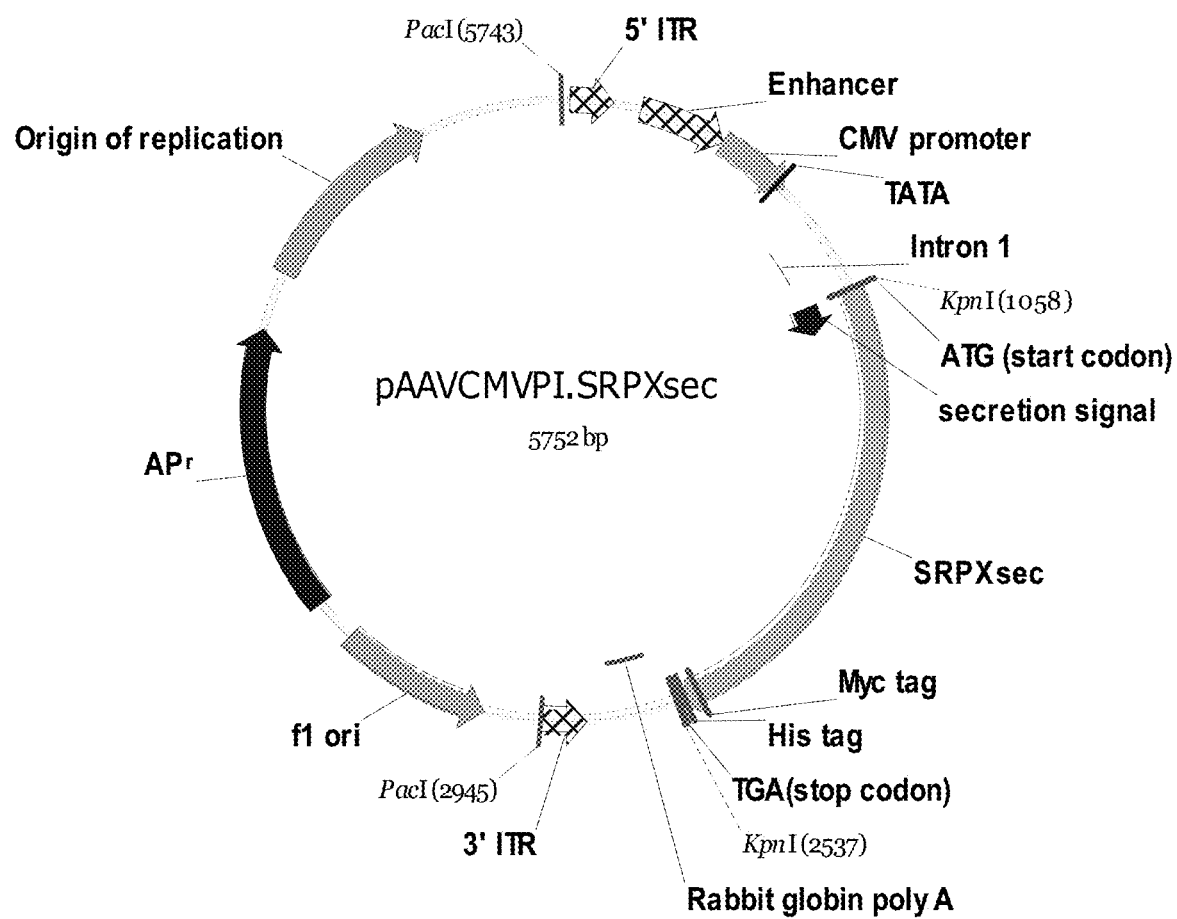
FIG. 4A is a plasmid map of pAAVCMVPI.SRPXsec.
Figure 4B:
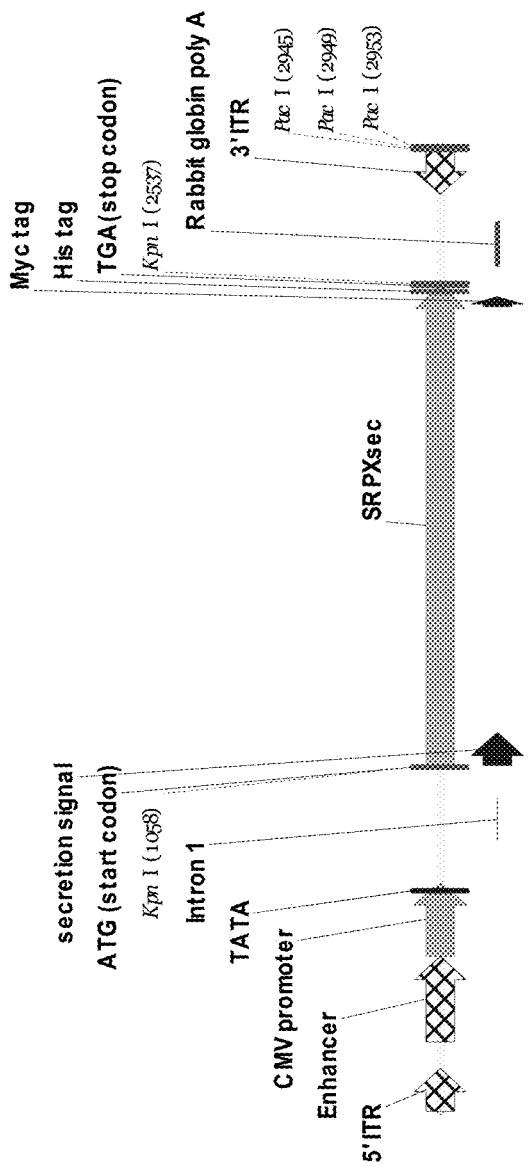
FIG. 4B is a map of adeno-associated vector AAV-SRPXsec.

An exemplary AAV vector containing a polypeptide that includes SEQ ID NO:1 is shown in FIG. 4B and has the sequence:

(SEQ ID NO: 3)
attaggctgcgcgctcgctcgctcactgaggccgcccgggcaaagcccgg gcgtcgggcgacctttggtcgcccggcctcagtgagcgagcgagcgcgca gagagggagtggccaactccatcactaggggttccttgtagttaatgatt aacccgccatgctacttatctaccagggtaatggggatcctctagaacta tagctagcatgcctgcaggctgaccgcccaacgaccccgcccattgacg tcaataatgacgtatgttcccatagtaacgccaatagggactttccattg acgtcaatgggtggagtatttacggtaaactgcccacttggcagtacatc aagtgtatcatatgccaagtccgcccctattgacgtcaatgacggtaaa tggcccgcctggcattatgcccagtacatgaccttacgggactttcctac ttggcagtacatctacgtattagtcatcgctattaccatggtgatgcggt tttggcagtacaccaatgggcgtggatagcggtttgactcacggggattt ccaagtctccacccccattgacgtcaatgggagtttgttttggcaccaaa tcaacgggactttccaaaatgtcgtaataaccccgccccgttgacgcaaa tgggcggtaggcgtgtacggtgggaggtctatataagcagagctcgttta gtgaaccgtcagatcactagaagctttattgcggtagtttatcacagtta aattgctaacgcagtcagtgcttctgacacaacagtctcgaacttaagct gcagaagttggtcgtgaggcactgggcaggtaagtatcaaggttacaaga caggtttaaggagaccaatagaaactgggcttgtcgagacagagaagact cttgcgtttctgataggcacctattggtcttactgacatccactttgcct ttctctccacaggtgtccactcccagttcaattacagctcttaaggctag agtacttaatacgactcactataggctagcctcgagaattcacgcgtggt acggtaccatgatggagacagacacactcctgctatgggtactgctgctc tgggttccaggttccactggtgacgcggcccagccggccaggcgcgcgcg ccgtacgaagcttgactcaccactagaagacgatgaagtcgggtattcac acctagatataaagataccccgtggtgctcccccatcaaggtgaagtat ggggatgtgtactgcagggcccctcaaggaggatactacaaaacagccct gggaaccaggtgcgacattcgctgccagaagggctacgagctgcatggct

```
cttccctactgatctgccagtcaaacaaacgatggtctgacaaggtcatc
tgcaaacaaaagcgatgtcctacccttgccatgccagcaaatggagggtt
taagtgtgtagatggtgcctactttaactcccggtgtgagtattattgtt
caccaggatacacgttgaaaggggagcggaccgtcacatgtatggacaac
aaggcctggagcggccggccagcctcctgtgtggatatggaacctcctag
aatcaagtgcccaagtgtgaaggaacgcattgcagaacccaacaaactga
cagtccgggtgtcctgggagacacccgaaggaagagacacagcagatgga
attcttactgatgtcattctaaaaggcctccccccaggctccaacttttcc
agaaggagaccacaagatccagtacacagtctatgacagagctgagaata
agggcacttgcaaatttcgagttaaagtaagagtcaaacgctgtggcaaa
ctcaatgccccagagaatggttacatgaagtgctccagcgacggtgataa
ttatggagccacctgtgagttctcctgcatcggcggctatgagctccagg
gtagccctgcccgagtatgtcaatccaacctggcttggtctggcacggag
cccacctgtgcagccatgaacgtcaatgtgggtgtcagaacggcagctgc
acttctggatcagttttatgagaaaaggagactcctcattgtgtccacac
ccacagcccgaaacctcctttaccggctccagctaggaatgctgcagcaa
gcacagtgtggccttgatcttcgacacatcaccgtggtggagctggtggg
tgtgttcccgactctcattggcaggataggagcaaagattatgcctccag
ccctagcgctgcagctcaggctgttgctgcgaatcccactctactccttc
agtatggtgctagtggataagcatggcatggacaaagagcgctatgtctc
cctggtgatgcctgtggccctgttcaacctgattgacacttttcccttga
gaaaagaagagatggtcctacaagccgaaatgagccagacctgtaacacc
gctcgaggagggcccgaacaaaaactcatctcagaagagaatctgaatag
cgccgtcgaccatcatcatcatcatcattgaggtaccctctagagtcgac
ccgggcggcctcgaggacggggtgaactacgcctgaggatccgatcttt
tccctctgccaaaaattatggggacatcatgaagcccttgagcatctga
cttctggctaataaaggaaatttattttcattgcaatagtgtgttggaat
ttttgtgtctctcactcggaagcaattcgttgatctgaatttcgaccac
ccataatacccattaccctggtagataagtagcatggcgggttaatcatt
aactacaaggaaccctagtgatggagttggccactccctctctgcgcgc
tcgctcgctcactgaggccgggcgaccaaggtcgcccgacgcccgggct
tgcccgggcggcctcagtgagcgagcgagcgcgcagccttaattaatta
attaaggcctta
```

Figure 5A:
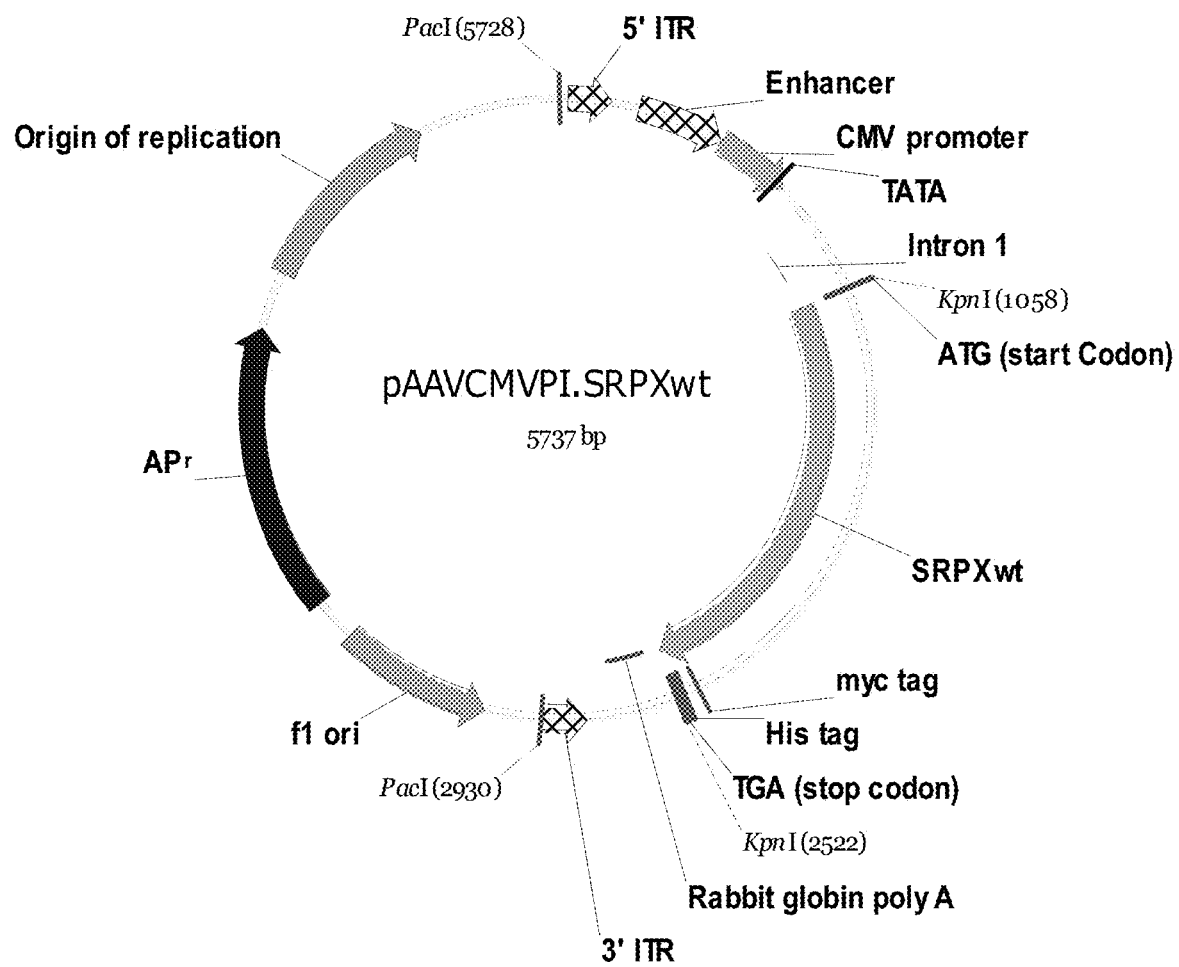
FIG. 5A is a plasmid map of pAAVCMVPI.SRPXwt.
Figure 5B:
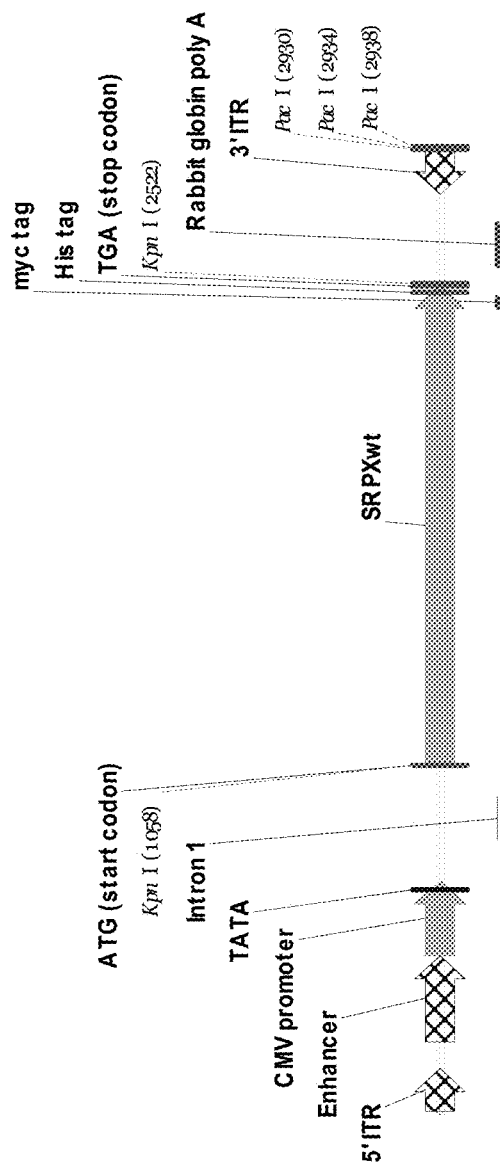
FIG. 5B is a map of adeno-associated vector AAV-SRPXwt.

An exemplary AAV vector containing a polypeptide that includes SEQ ID NO:2 is shown in FIG. 5B and has the sequence:

(SEQ ID NO: 4)
```
attaggctgcgcgctcgctcgctcactgaggccgcccgggcaaagcccgg
gcgtcgggcgacctttggtcgcccggcctcagtgagcgagcgagcgcgca
gagagggagtggccaactccatcactaggggttccttgtagttaatgatt
aacccgccatgctacttatctaccagggtaatggggatcctctagaacta
tagctagcatgcctgcaggctgaccgcccaacgaccccgcccattgacg
tcaataatgacgtatgttcccatagtaacgccaatagggactttccattg
acgtcaatgggtggagtatttacggtaaactgcccacttggcagtacatc
aagtgtatcatatgccaagtccgcccctattgacgtcaatgacggtaaa
tggcccgcctggcattatgcccagtacatgaccttacgggactttcctac
ttggcagtacatctacgtattagtcatcgctattaccatggtgatgcggt
tttggcagtacaccaatgggcgtggatagcggtttgactcacggggattt
ccaagtctccacccccattgacgtcaatgggagtttgttttggcaccaaaa
tcaacgggactttccaaaatgtcgtaataaccccgccccgttgacgcaaa
tgggcggtaggcgtgtacggtgggaggtctatataagcagagctcgttta
gtgaaccgtcagatcactagaagctttattgcggtagtttatcacagtta
aattgctaacgcagtcagtgcttctgacacaacagtctcgaacttaagct
gcagaagttggtcgtgaggcactgggcaggtaagtatcaaggttacaaga
caggtttaaggagaccaatagaaactgggcttgtcgagacagagaagact
cttgcgtttctgataggcacctattggtcttactgacatccactttgcct
ttctctccacaggtgtccactcccagttcaattacagctcttaaggctag
agtacttaatacgactcactataggctagcctcgagaattcacgcgtggt
acggtaccatggggagccccgcacatcggcccgcgctgctgctgctgctg
ccgcctctgctgctgctgctgctgcgcgtcccgcccagccgcagctt
cccaggatcgggagactcaccactagaagacgatgaagtcgggtattcac
accctagatataaagatacccgtggtgctcccccatcaaggtgaagtat
ggggatgtgtactgcagggcccctcaaggaggatactacaaaacagccct
gggaaccaggtgcgacattcgctgccagaagggctacgagctgcatggct
cttccctactgatctgccagtcaaacaaacgatggtctgacaaggtcatc
tgcaaacaaaagcgatgtcctacccttgccatgccagcaaatggagggtt
taagtgtgtagatggtgcctactttaactcccggtgtgagtattattgtt
caccaggatacacgttgaaaggggagcggaccgtcacatgtatggacaac
aaggcctggagcggccggccagcctcctgtgtggatatggaacctcctag
aatcaagtgcccaagtgtgaaggaacgcattgcagaacccaacaaactga
cagtccgggtgtcctgggagacacccgaaggaagagacacagcagatgga
attcttactgatgtcattctaaaaggcctccccccaggctccaacttttcc
agaaggagaccacaagatccagtacacagtctatgacagagctgagaata
agggcacttgcaaatttcgagttaaagtaagagtcaaacgctgtggcaaa
ctcaatgccccagagaatggttacatgaagtgctccagcgacggtgataa
ttatggagccacctgtgagttctcctgcatcggcggctatgagctccagg
gtagccctgcccgagtatgtcaatccaacctggcttggtctggcacggag
cccacctgtgcagccatgaacgtcaatgtgggtgtcagaacggcagctgc
acttctggatcagttttatgagaaaaggagactcctcattgtgtccacac
ccacagcccgaaacctcctttaccggctccagctaggaatgctgcagcaa
gcacagtgtggccttgatcttcgacacatcaccgtggtggagctggtggg
tgtgttcccgactctcattggcaggataggagcaaagattatgcctccag
```

-continued

```
ccctagcgctgcagctcaggctgttgctgcgaatcccactctactccttc agtatggtgctagtggataagcatggcatggacaaagagcgctatgtctc cctggtgatgcctgtggccctgttcaacctgattgacacttttcccttga gaaagaagagatggtcctacaagccgaaatgagccagacctgtaacacc gaacaaaactcatctcagaagaggatctgaatagcgccgtcgaccatca tcatcatcatcattgaggtaccctctagagtcgacccgggcggcctcgag gacggggtgaactacgcctgaggatccgatcttttccctctgccaaaaa ttatgggacatcatgaagcccttgagcatctgacttctggctaataaa ggaaatttattttcattgcaatagtgtgttggaattttttgtgtctctca ctcggaagcaattcgttgatctgaatttcgaccacccataatacccatta ccctggtagataagtagcatggcgggttaatcattaactacaaggaaccc ctagtgatggagttggccactccctctctgcgcgctcgctcgctcactga ggccgggcgaccaaaggtcgcccgacgcccgggctttgcccgggcggcct cagtgagcgagcgagcgcgcagccttaattaattaattaaggcctta
```

In some embodiments, a nucleic acid that expresses a SRPX polypeptide is administered directly to cancer cells or to cells in the vicinity of the cancer cells. In some embodiments, a nucleic acid that expresses a SRPX polypeptide is administered to a cell ex vivo, which is then administered to the subject in the vicinity of the tumor.

A SRPX agent can be produced by any means known in the art, e.g., by chemical synthesis, recombinant methods, or isolation from cells that naturally produce SRPX. Methods of purification and isolation of molecules that include polypeptides are also well known to those of skill in the art.

Production of Fragments and Analogs of SRPX

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of the mutagenized DNA produces polypeptide fragments. Digestion with "end-nibbling" endonucleases can thus generate DNAs that encode an array of fragments. DNAs that encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention can be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments is inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants that include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis can be conducted at the target codon or region and the expressed desired protein subunit variants are screened for the optimal combination of desired activity.

Oligonucleotide Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* (1978) USA, 75: 5765).

Cassette Mutagenesis

Another method for preparing variants, cassette mutagenesis, is based on the technique described by Wells et al. (*Gene* (1985) 34:315). The starting material is a plasmid (or other vector) that includes the protein subunit DNA to be mutated. The codon(s) in the protein subunit DNA to be mutated are identified. There must be a unique restriction endonuclease site on each side of the identified mutation site(s). If no such restriction sites exist, they can be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids that appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., inhibition of growth of human cancer cell lines (e.g., NCI-H23, EKVX, HOP-62, HOP-92, HCT-15, SW-620, COL0205, HT29, HCT-116, KM-12, CCRF-CEM, K-562, MOLT-4, SR, RPMI-8226, A549-ATCC, NCI-H226, NCI-H322M) is measured. Each of the techniques described below is amenable to high through-put analysis for screening large numbers of sequences created, e.g., by random mutagenesis techniques.

Cancers

The new methods can be used to treat several types of cancer, e.g., lung cancers (e.g., adenocarcinoma, nonsmall cell lung cancer), colorectal cancers, thyroid cancers (e.g., papillary thyroid carcinoma, anaplastic thyroid carcinoma, follicular carcinoma, follicular adenoma), lymphomas (e.g., non-Hodgkin lymphoma), multiple myeloma, leukemias, breast cancers, ovarian cancers, gastric cancers, bladder cancers, pancreatic cancers, gall bladder cancers, bile duct cancers, and other carcinomas. In some embodiments, the present methods can be used to treat a subject having an epithelial cancer, e.g., a solid tumor of epithelial origin, e.g., lung, breast, ovarian, prostate, renal, pancreatic, or colon cancer. Methods of diagnosing cancers are well known to those of skill in the art.

In addition, the methods described herein can include identifying the cancer as lacking SRPX expression. A number of methods for detecting levels of SRPX expression are known in the art. In some embodiments, levels of SRPX mRNA are detected in cells from the tumor; alternatively or in addition, levels or SRPX polypeptide are detected in a sample comprising tissue or cells from the tumor. See, e.g., Yamashita et al. 1999, Oncogene 18:4777; Tambe et al. 2009, Cancer Lett 283:74; Kim et a. 2003, Hum Pathol 34:654; Mukaisho et al. 2002, Jpn J Cancer Res 93:888; Shimakage et al. 2000, Int J Cancer 87:5; Shimakage et al. 2002, Hum Pathol 33:615; Shimakage et al. 2009, Oncol Rep 21:1367; and Tambe et al. 2007, Carcinogenesis 28(4): 777-784, all of which are incorporated herein by reference.

Pharmaceutical Formulations

The SRPX agents described herein (all of which can be referred to herein as "active compounds"), can be incorporated into pharmaceutical compositions. Such compositions typically include the active compound and a pharmaceutically acceptable carrier or excipient. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

There are a number of methods by which the new compositions for use in the new methods can be delivered to subjects, in general, and to specific cells or tissue in those subjects, in particular. For example, a SRPX agent (e.g., a polypeptide or active fragment thereof) as described herein can be injected into a subject or a tissue of the subject. In another example, a vector (e.g., a plasmid or virus) encoding a SRPX agent can be introduced into a cell or tissue of the subject. The vector would then enter the cell or cells in that tissue and express the SRPX agent. Delivery specificity of such plasmids can be enhanced by associating them with organ- or tissue-specific affinity, so that they preferentially enter specified cell types; in preferred embodiments, the vector would enter cells in or near the tumor. Because SRPX can act extracellularly, it is not necessary to deliver the vector directly to tumor cells. The vector can be delivered to the tissue surrounding the tumor, or cells expressing and secreting SRPX can be delivered to a site near the tumor. Similarly, when SRPX polypeptides or active fragments thereof are administered, the active agents need not enter the cells, but are delivered to the extracellular surface. Methods of expressing proteins for tumor therapy are described, e.g., in Cross and Burmester, 2006, Clin. Med. Res., 4:218-227; Lejuene et al., 2007, Expert Rev. Anticancer Ther. 7:701-713; and Bloquel et al., 2004, J. Gene Med., 6:S11-S23.

Compounds and their physiologically acceptable salts and solvates can be formulated for oral, topical, buccal, parenteral or rectal administration or administration by inhalation or insufflation (either through the mouth or the nose).

The compounds will generally be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, for example, sterile pyrogen-free water, before use. Where the compositions are intended for use in a specific treatment area, the compositions can be administered by one or more local injections into the tumor site to diminish as much as possible any side effects relating to the compound's activities outside of the treatment area.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt. A depot preparation can include embedded or encapsulated cells or tissue that secrete a SRPX agent, which can be administered, e.g., by implantation or by intramuscular injection.

The compositions can, if desired, be presented in a pack or dispenser device that can contain one or more unit dosage forms containing the active ingredient. The pack can, for example, include metal or plastic foil, such as a blister pack. The pack or dispenser device can be accompanied by instructions for administration.

The therapeutic compositions of the invention can also contain a carrier or excipient, many of which are known to skilled artisans. Methods for making such formulations are well known and can be found in, for example, Remington: The Science and Practice of Pharmacy, University of the Sciences in Philadelphia (USIP), 2005.

The SRPX-encoding nucleic acid compositions can also be formulated for intracellular delivery of the active compounds, using methods known in the art. For example, the compositions can include liposomes or other carriers that deliver the active compound across the plasma membrane. Vesicles that are covered with membrane-permeant peptides, such as Tat or Antennapedia, can also be used. A number of other methods for enhancing intracellular delivery are familiar to those of skill in the art. Such methods are not needed when the SRPX polypeptides or fragments thereof are used, as the SRPX polypeptides act extracellularly, and are thus delivered to the extracellular surface of the tumor cells. Thus in some embodiments, the methods include the use of a composition comprising a SRPX polypeptide or active fragment thereof, but not including any cell membrane permeation-enhancing compounds, e.g., the composition does not include liposomes or membrane-permeant peptides.

It is recognized that the pharmaceutical compositions and methods described herein can be used independently or in combination with one another. That is, subjects can be administered one or more of the pharmaceutical compositions, e.g., pharmaceutical compositions that include a SRPX agent, subjected to one or more of the therapeutic methods described herein, or both, in temporally overlapping or non-overlapping regimens. When therapies overlap temporally, the therapies can generally occur in any order and can be simultaneous (e.g., administered simultaneously together in a composite composition or simultaneously but as separate compositions) or interspersed.

By way of example, a subject afflicted with a disorder described herein can be simultaneously or sequentially administered both a cytotoxic agent which selectively kills aberrant cells and an antibody (e.g., an antibody of the invention) which can, in one embodiment, be conjugated or linked with a therapeutic agent, a cytotoxic agent, an imaging agent, or the like.

Effective Doses

Toxicity and therapeutic efficacy of a SRPX agent can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Inhibitors that exhibit large therapeutic indices are preferred. While inhibitors that exhibit toxic side effects can be used, care can be taken to design a delivery system that targets such compounds to the site of affected tissue to minimize potential damage to non-target cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the new methods, the therapeutically effective dose can be estimated initially from cell culture assays. A dose can also be calculated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans.

EXAMPLES

Example 1. SRPX Inhibits the Growth of Cancer Cells and Lung Cancer Xenografts Quantitative reverse transcription-polymerase chain reaction (qRT-PCR) analysis was performed to monitor SRPX expression in 9 normal lung samples, 14 lung adenocarcinoma samples, and 6 lung squamous cell carcinoma samples. Total RNA from the human samples was obtained from the University of Massachusetts Medical School Cancer Center Tissue Bank. Reverse transcription was performed using SuperScript™ II Reverse Transcriptase (Invitrogen) and an oligo(dT) primer (Invitrogen), followed by quantitative PCR using Fast SYBR™ Green Master Mix (Applied Biosystems) and gene-specific primers for SRPX. For each sample, expression of glyceraldehyde 3-phosphate dehydrogenase (GAPDH) provided an internal normalization control. For normal lung samples, the average of the 9 samples is shown. Error bars indicate standard deviation. SRPX expression was significantly decreased relative to normal lung tissue in all squamous cell carcinoma samples and at least 13 of 14 lung adenocarcinoma samples (FIG. 1A).

Figure 1B:
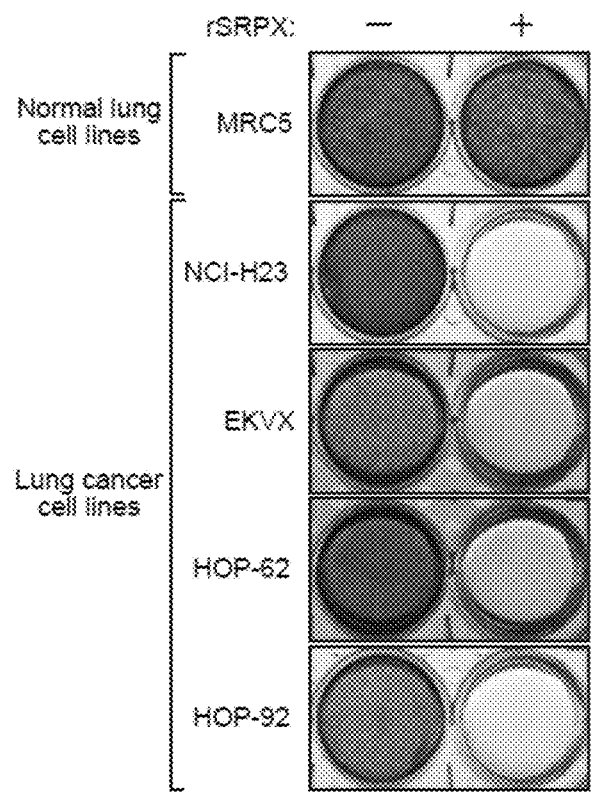
FIG. 1B is a photograph showing growth of a normal lung cell line (MRCS) and lung cancer cell lines (NCH-H23, EKVX, HOP-62, and HOP-92) grown in the presence (+) or absence (−) of rSRPX.

To determine if SRPX could affect growth of cancer cells, several lung cancer cell lines and, as a control, the normal lung cell line MRCS, were plated in 6-well plates ($3 \times 10^5$ cells per well), treated with or without 10 μg/ml recombinant SRPX (rSRPX) and stained with crystal violet. To express and purify rSRPX, an SRPXsec expression construct including a nucleic acid encoding SEQ ID NO:1 with a heterologous signal sequence and Myc and $His_6$ tags was transfected into FreeStyle™ Chinese Hamster Ovary (CHO) cells (Invitrogen), and conditioned medium was collected 96 hours later and incubated with TALON™ Metal Affinity Resin (Clontech) to purify the $His_6$-tagged SRPX protein. The purified protein was dialyzed in phosphate buffered saline (PBS) to remove free salts. rSRPX decreased growth of the cancer cell lines tested but had no effect on the growth of the normal lung cell line (FIG. 1B).

Figure 1C:
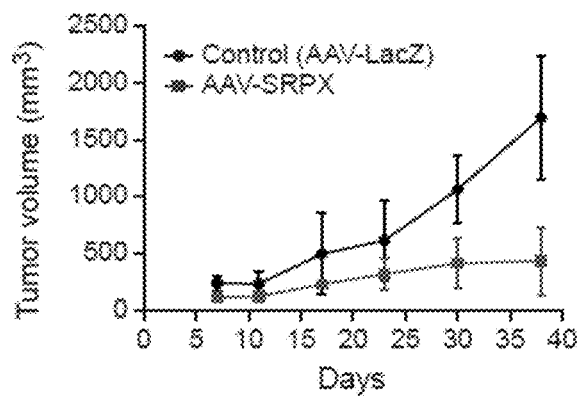
FIGS. 1C and 1D are line graphs depicting tumor growth in mice with tumor xenografts treated with a control vector (AAV-LacZ) or a vector expressing SRPX (AAV-SRPX).

To investigate the effect of SRPX on tumors in vivo, $5 \times 10^6$ A549 human alveolar adenocarcinoma cells (mixed with Matrigel™ matrix in a volume of 100 μl) were injected subcutaneously into the right flank of female BALB/c nu/nu (nude) mice (n=2 mice per experimental group). Three days later, the mice were injected into the anterior tibialis muscle of the left leg with either $3.0 \times 10^{11}$ particles of AAV-SRPXwt or, as a control, AAV-LacZ. Tumor dimensions were measured on days 7, 11, 17, 23, 30 and 38 after injection, and tumor volume was calculated using the formula $\pi/6 \times$ (length)×(width). Error bars indicate standard deviation. AAV-SRPX significantly reduced tumor growth at days 30 and 38 as compared to the control (FIG. 1C).

Figure 1D:
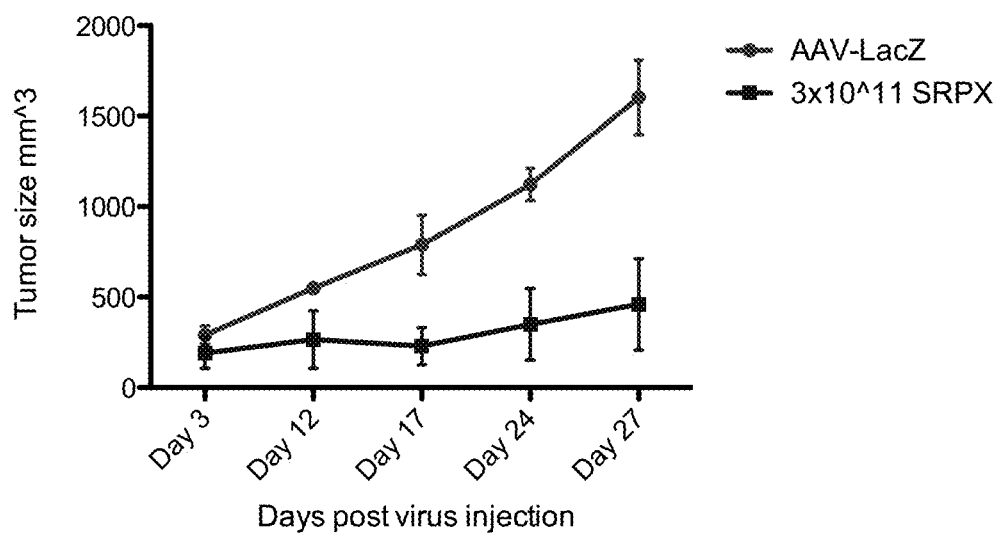

In another experiment, about $10^6$ A549 cells were injected in Balb/c Nu/Nu mice, and AAv9-SRPX virus was injected when the tumors reached the size of 250 mm³. The results, shown in FIG. 1D, are for two mice per group as one animal in the control group failed to develop the tumor and one animal in SRPX group developed an abnormal mass around the belly. The difference in tumor growth is very significant.

Figure 1E:
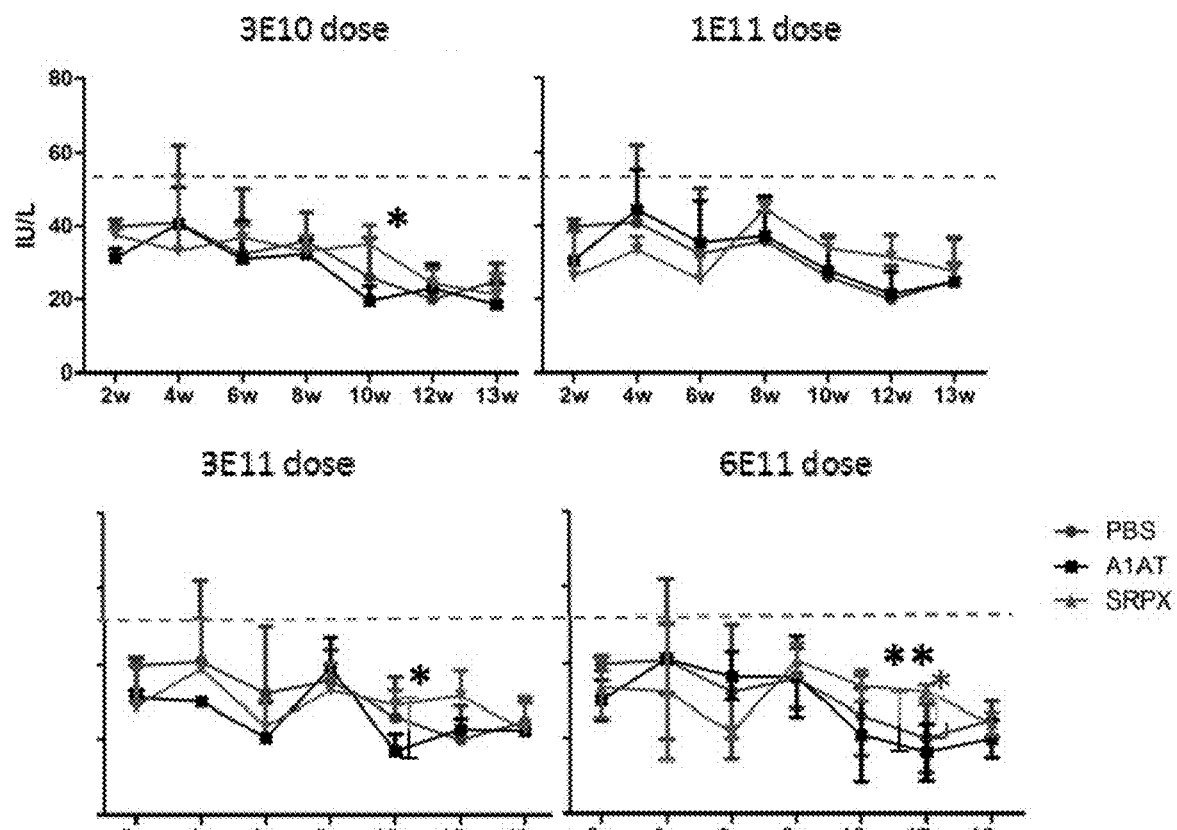
FIGS. 1E and 1F are line graphs showing levels of alanine aminotransferase (ALT, 1E) and aspartate aminotransferase (AST, 1F) in animals administered the indicated doses of SRPX. No significant increases were seen in either ALT or AST.
Figure 1F:
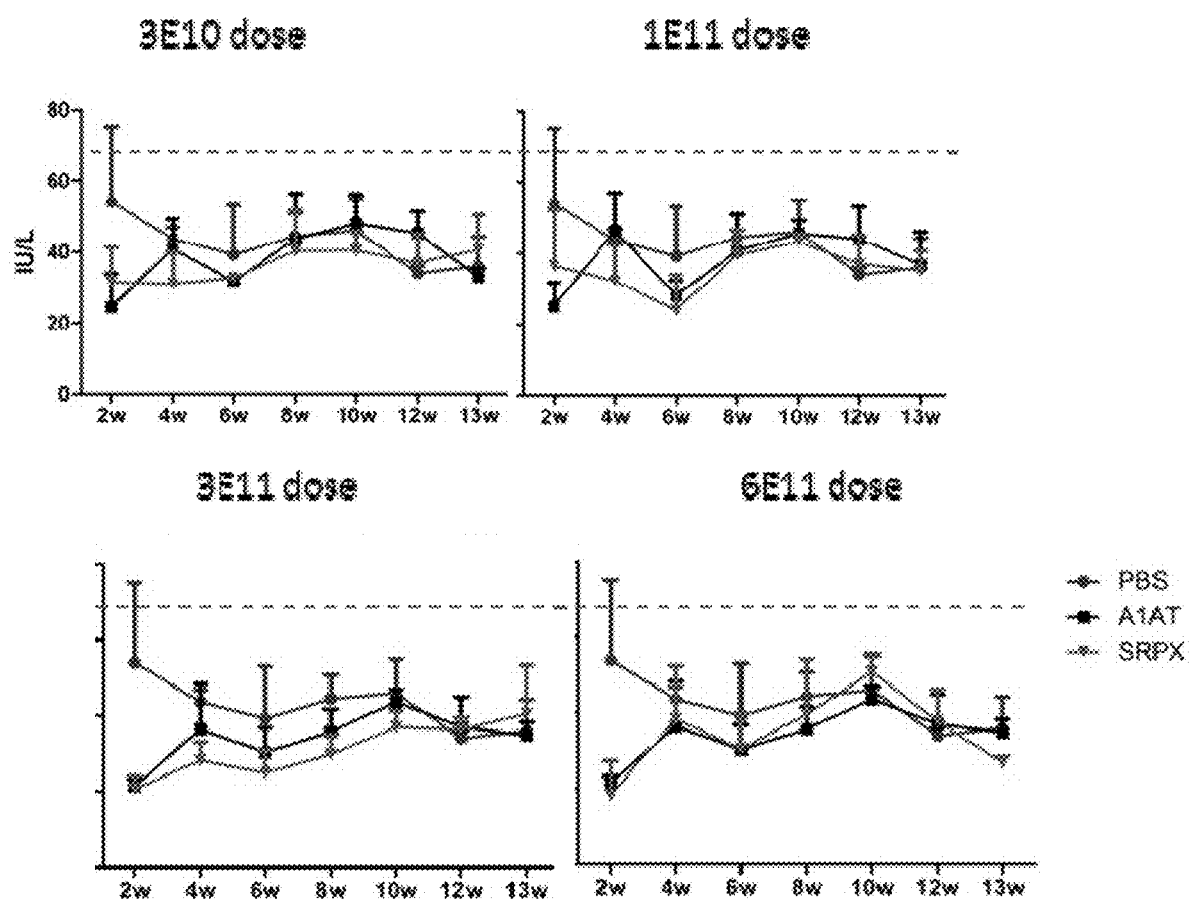

To determine whether in vivo administration of SRPX was associated with significant toxicity, increasing doses were administered to mice and levels of liver enzymes, aspartate aminotransferase (AST) and alanine aminotransferase (ALT), increases in which are typically associated with toxic insult, were measured. The results, as shown in FIGS. 1E (ALT) and 1F (AST), demonstrated that SRPX has no detectable liver toxicity at the doses tested.

Figure 2:
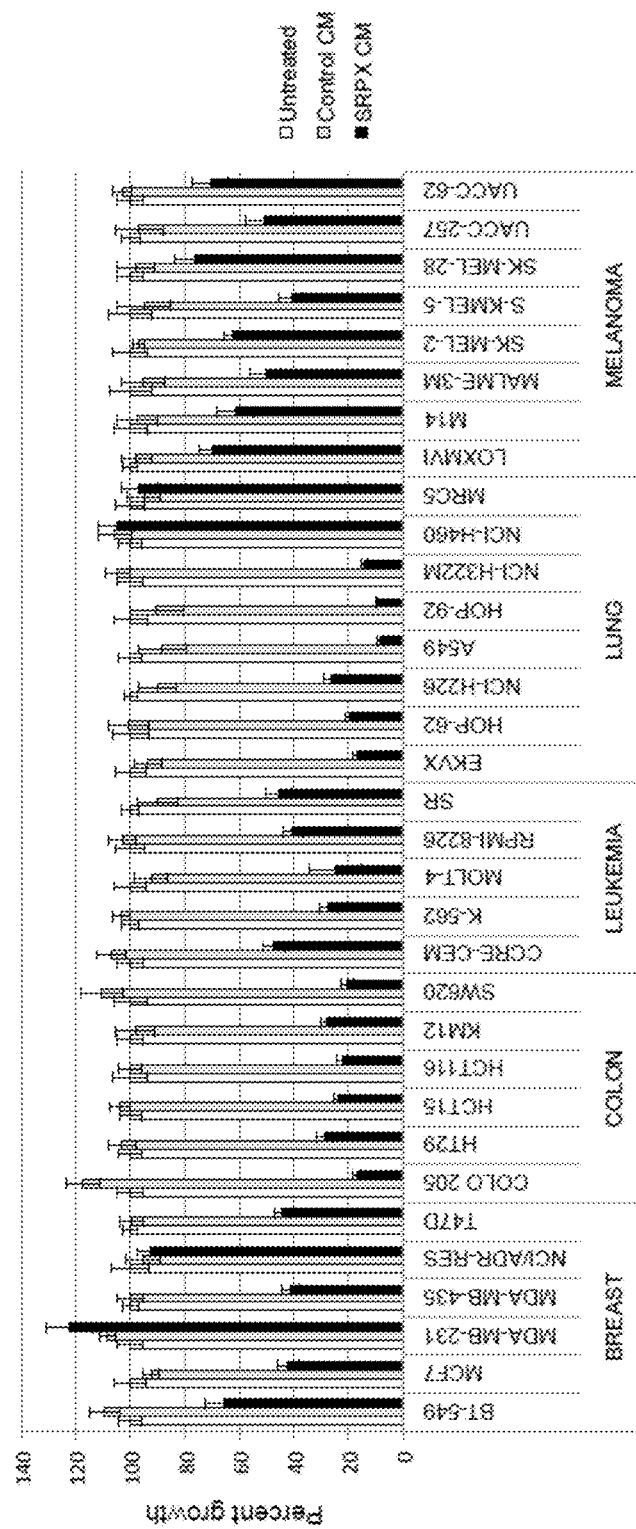
FIG. 2 is a bar graph depicting relative growth of breast, colon, leukemia, lung, and melanoma cancer cell lines without treatment or treated with control conditioned media (CM) or CM containing SRPX.

The NCI60 panel of human cancer cell lines (see Shoemaker, 2006, Nat. Rev. Cancer, 6:813-823) was obtained from the National Cancer Institute. The panel includes cell lines corresponding to breast (MDA-MB-231, HS 578T, BT-549, T47-D, MCF7), ovarian (NCI-ADR-RES, OVCAR-3, OVCAR-5, OVCAR-8, OVCAR-4, SK-OV-3, IGROV1), prostate (DU-145, PC-3), renal (TK-10, CAKI-1, A496, ACHN, RXF-393, 786-0, SN12C, UO-31), non-small-cell lung (NCI-H460, HOP-62, A549-ATCC, NCI-H226, EKVX, NCI-H322M, HOP-92, NCI-H522), central nervous system (CNS) (SF-295, SF-268, SF-539, SNB-19, SNB-75, U251), colon (HCT-15, SW-620, COLO205, HT29, HCC-2998, HCT-116, KM-12), melanoma (SK-MEL-28, SK-M2L-2, LOX IMVI, M14, MALM-3M, SK-MEL-5, UACC-257, UACC-62, MDA-MB-435), and hematopoietic (CCRF-CEM, K-562, MOLT-4, SR, RPMI-8226) cancers (only a subset of the NCI60 panel is shown). Cells ($3 \times 10^5$ for breast, colon, leukemia, lung cell lines, and 2×105 for melanoma cell lines) were plated and treated with 30% control CM or SRPX-containing CM (produced as described above for FIG. 1B), or left untreated. After 3 days, the CM was replaced with complete medium, and the cells allowed were to grow for an additional 4 days before staining with crystal violet. Percent growth was calculated relative to the untreated control cells, which was set to 100%. Error bars indicate standard deviation. The results show that in addition to lung cancer, SRPX inhibits the growth of several other cancer cell types, including breast cancer, colon cancer, and leukemia cell lines (FIG. 2).

Figure 3A:
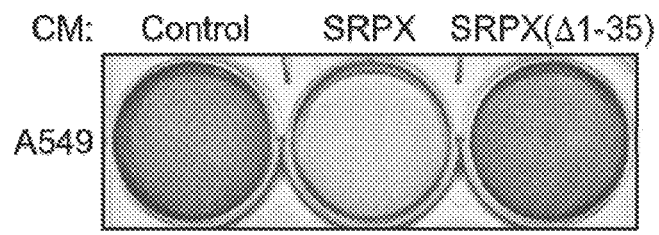
FIG. 3A is a photograph showing growth of a human lung adenocarcinoma cell line (A549) treated in the presence of control CM, SRPX-containing CM or SRPX(Δ1-35)-containing CM.
Figure 3B:
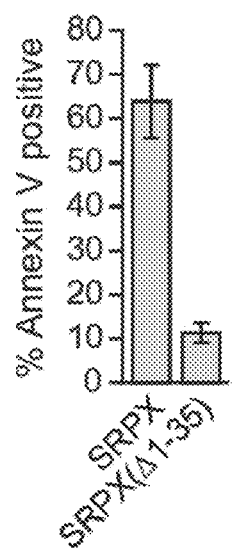
FIG. 3B is a bar graph depicting the percent apoptosis, as assessed by Annexin V staining, in A549 cells transfected with a vector expressing SRPX or SRPX(Δ1-35).
Figure 3C:
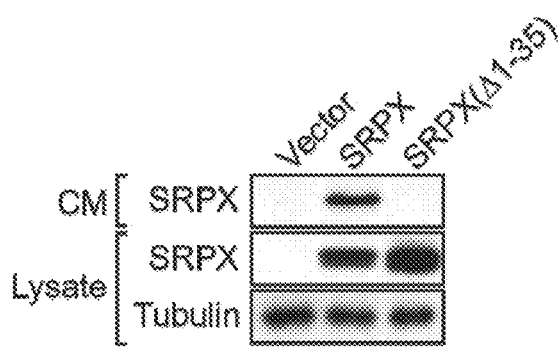
FIG. 3C is an immunoblot showing expression of SRPX and SRPX(Δ1-35) in cell lysate and CM.

As a secreted protein, SRPX contains an N-terminal signal sequence that directs its secretion. To determine whether the signal sequence is required for the ability of SRPX to inhibit cancer cell growth, a derivative of full-length SRPX that lacks the N-terminal signal sequence (amino acids 1-35; hereafter called SRPX(Δ1-35)) was constructed and tested for its ability to inhibit growth of A549 human lung adenocarcinoma epithelial cells. Briefly, $3 \times 10^5$ A549 cells were plated in 6-well plates and treated with 30% CM derived from cells expressing either empty vector (control), full-length SRPX or SRPX(Δ1-35). After 3 days, the CM was replaced with complete medium, and the cells were allowed to grow for an additional 4 days before staining with crystal violet. The results show that in contrast to full-length SRPX, SRPX(Δ1-35) does not inhibit growth of A549 cells (FIG. 3A). To confirm these results, the ability of SRPX(Δ1-35) was analyzed for its ability to kill A549 cells using an apoptosis assay. A549 cells (1.5×10⁶) were transfected with a construct expressing either full-length SRPX or SRPX(Δ1-35), and 48 hours later were stained with Annexin V and 7 AAD (BD Bioscience) and analyzed by fluorescence-activated cell sorting (FACS). The results show that SRPX(Δ1-35) did not induce apoptosis compared to full-length SRPX. Immunoblot analysis confirmed that SRPX(Δ1-35) is expressed at roughly equivalent levels to full-length SRPX but, as expected, is not secreted into the CM (FIG. 3C). Collectively, the results show that secretion of SRPX is required for cell killing and that SRPX mediates cell killing extracellularly.

These results strongly support the use of SRPX to treat and prevent a wide range of cancers, including lung cancers, colon cancers, and leukemias.

Other Embodiments

A number of embodiments of the invention have been described. Nevertheless, it will be understood that various modifications may be made without departing from the spirit and scope of the invention. Accordingly, other embodiments are within the scope of the following claims.

---

What is claimed is:

1. A method of treating a solid tumor in a mammalian subject, the method comprising:
   identifying the mammalian subject having the solid tumor; and
   administering to the subject an effective amount of a nucleic acid encoding a polypeptide that is at least 80% identical to SEQ ID NO:1, thereby treating the solid tumor.

2. The method of claim 1, wherein the nucleic acid is systemically administered.

3. The method of claim 1, wherein the nucleic acid is parenterally administered.

4. The method of claim 1, wherein the nucleic acid is intramuscularly injected.

5. The method of claim 1, wherein the solid tumor is a cancer.

6. The method of claim 5, wherein the cancer is a carcinoma.

7. The method of claim 5, wherein the cancer is a lung adenocarcinoma.

8. The method of claim 5, wherein the cancer is a breast cancer, bladder cancer, ovarian cancer, pancreatic cancer, colon cancer, colorectal carcinoma, or papillary thyroid carcinoma.

9. The method of claim 1, wherein the polypeptide is at least 90% identical to SEQ ID NO: 1.

10. The method of claim 1, wherein the polypeptide is at least 95% identical to SEQ ID NO: 1.

11. The method of claim 1, wherein the nucleic acid is in a viral vector.

12. The method of claim 11, wherein the viral vector is an adenovirus, adeno-associated virus (AAV), retrovirus, or lentivirus vector.

13. The method of claim 12, wherein the viral vector is an AAV vector.

14. The method of claim 13, wherein the AAV vector comprises a nucleic acid sequence that is at least 80% identical to SEQ ID NO: 3.

15. The method of claim 1, wherein the nucleic acid is in a virus.

16. The method of claim 15, wherein the virus is an adenovirus, adeno-associated virus (AAV), parvovirus, lentivirus, retrovirus, or herpes simplex virus.

17. The method of claim 16, wherein the virus is an AAV.

18. The method of claim 17, wherein the AAV is an AAV9 virus.

* * * * *